US009575059B2

(12) United States Patent
Kshirsagar et al.

(10) Patent No.: US 9,575,059 B2
(45) Date of Patent: Feb. 21, 2017

(54) LANTHANUM-BASED CONCENTRATION AGENTS FOR MICROORGANISMS

(71) Applicant: 3M INNOVATIVE PROPERTIES COMPANY, St. Paul, MN (US)

(72) Inventors: Manjiri T. Kshirsagar, Woodbury, MN (US); Evan Koon Lun Yuuji Hajime, Woodbury, MN (US); Andrew W. Rabins, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 87 days.

(21) Appl. No.: 14/400,390

(22) PCT Filed: May 23, 2013

(86) PCT No.: PCT/US2013/042359
§ 371 (c)(1),
(2) Date: Nov. 11, 2014

(87) PCT Pub. No.: WO2013/184373
PCT Pub. Date: Dec. 12, 2013

(65) Prior Publication Data
US 2015/0132740 A1    May 14, 2015

Related U.S. Application Data

(60) Provisional application No. 61/655,601, filed on Jun. 5, 2012.

(51) Int. Cl.
| | | |
|---|---|---|
| *G01N 33/53* | (2006.01) | |
| *G01N 33/569* | (2006.01) | |
| *B01J 20/02* | (2006.01) | |
| *B01J 20/28* | (2006.01) | |
| *C12N 1/14* | (2006.01) | |
| *C12Q 1/04* | (2006.01) | |
| *C12Q 1/24* | (2006.01) | |
| *C12N 11/14* | (2006.01) | |

(52) U.S. Cl.
CPC ....... *G01N 33/5306* (2013.01); *B01J 20/0277* (2013.01); *B01J 20/28026* (2013.01); *B01J 20/28028* (2013.01); *C12N 11/14* (2013.01); *C12Q 1/04* (2013.01); *C12Q 1/24* (2013.01); *G01N 33/56916* (2013.01); *G01N 33/56938* (2013.01); *G01N 33/56961* (2013.01); *G01N 2333/245* (2013.01); *G01N 2333/395* (2013.01)

(58) Field of Classification Search
CPC ...... A61L 31/18; A61L 31/16; A61L 2300/44; A61L 31/10; A61L 2300/00; A61L 2300/416; A61L 2300/45; A61L 2300/608; A61L 31/082; B82Y 15/00; B82Y 20/00; B82Y 25/00; A61F 2/82; A61F 2210/009; A61F 2250/0067; B01J 20/041; B01J 20/06; B01J 20/10; B01J 20/14; B01J 20/3071; B01J 20/3204; B01J 20/3236; B01J 20/00; B01J 20/0277; B01J 20/28026; B01J 20/28028; C12N 11/14; C12N 1/02; C12Q 1/04; C12Q 1/24; G01N 1/40
See application file for complete search history.

(56) References Cited

U.S. PATENT DOCUMENTS

| | | |
|---|---|---|
| 5,238,812 A | 8/1993 | Coulter |
| 5,576,185 A | 11/1996 | Coulter |
| 5,603,838 A | 2/1997 | Misra |
| 6,957,743 B2 | 10/2005 | Johnston |
| 7,112,272 B2 | 9/2006 | Hughes |
| 7,112,280 B2 | 9/2006 | Hughes |
| 7,169,304 B2 | 1/2007 | Hughes |
| 7,419,601 B2 | 9/2008 | Cooper |
| 7,422,868 B2 | 9/2008 | Fan |
| 7,588,782 B2 | 9/2009 | Moerck |
| 8,546,100 B2 * | 10/2013 | Kshirsagar ............... B01J 20/02 435/174 |
| 9,029,100 B2 * | 5/2015 | Kshirsagar ....................... 435/34 |
| 2003/0156981 A1 | 8/2003 | Mills |
| 2003/0175207 A1 | 9/2003 | Olstein |
| 2006/0223070 A1 | 10/2006 | Wisniewski |
| 2008/0011662 A1 | 1/2008 | Milosavljevic |
| 2008/0053922 A1 | 3/2008 | Honsinger, Jr. |
| 2008/0089948 A1 | 4/2008 | Hallenbeck |
| 2009/0107925 A1 | 4/2009 | Burba, III |
| 2009/0111689 A1 | 4/2009 | Burba, III |
| 2010/0059443 A1 | 3/2010 | Brellisford |
| 2010/0062421 A1 | 3/2010 | Xia |
| 2010/0243542 A1 | 9/2010 | Burba, III |
| 2010/0255559 A1 | 10/2010 | Burba, III |
| 2011/0000854 A1 | 1/2011 | Nichols |
| 2011/0033337 A1 | 2/2011 | Burba, III |
| 2011/0123628 A1 | 5/2011 | Moerck |
| 2011/0280956 A1 | 11/2011 | Gore |
| 2011/0318410 A1 | 12/2011 | Moerck |
| 2013/0032529 A1 | 2/2013 | Hasslor |

FOREIGN PATENT DOCUMENTS

| | | |
|---|---|---|
| CN | 101012505 | 8/2007 |
| CN | 101695653 | 4/2010 |

(Continued)

OTHER PUBLICATIONS

Gerber, Phosphate starvation as an antimicrobial strategy: the controllable toxicity of lanthanum oxide nanoparticles, Chem. Commun. 2012, vol. 48, pp. 3869-3871. XP002700384.

(Continued)

*Primary Examiner* — Debbie K Ware
(74) *Attorney, Agent, or Firm* — Adrian L. Pishko; Jean A. Lown

(57) ABSTRACT

A concentration agent for microorganisms is provided that contains both lanthanum and carbonate. Additionally, articles that include the concentration agent and methods of concentrating a microorganism using the concentration agent are provided.

13 Claims, No Drawings

(56) References Cited

FOREIGN PATENT DOCUMENTS

| KR | 2008-0009668 | 1/2008 |
|---|---|---|
| WO | WO 2008-134472 | 11/2008 |
| WO | WO 2009-005590 | 1/2009 |
| WO | WO 2009-046183 | 4/2009 |
| WO | WO 2009-046191 | 4/2009 |
| WO | WO 2009-085357 | 7/2009 |
| WO | WO 2009-104890 | 8/2009 |
| WO | WO 2010-114725 | 10/2010 |
| WO | WO 2010-114727 | 10/2010 |
| WO | WO 2011-079038 | 6/2011 |
| WO | WO 2011-143475 | 11/2011 |
| WO | WO 2012-078374 | 6/2012 |
| WO | WO 2012-078426 | 6/2012 |

OTHER PUBLICATIONS

Jing, "Hemocompatibility and antibacterial properties of lanthanum oxide films synthesized by dual plasma deposition", Journal of Biomedical Materials Research, Dec. 15, 2008, vol. 87, No. 4, pp. 1027-1033.

Liu, "Efficient and Stable solid acid catalysts synthesized from sulfonation of swelling mesoporous polydivinylbenzenes", Journal of Catalysis, 2010, vol. 271, pp. 52-58.

Liu, "Unexpected Behavior of 1-Chlorodecane as a Novel Porogen in the Preparation of High-Porosity Poly (divinylbenzene) Microspheres", Journal of Physical Chemistry C, 2008, vol. 112, No. 34, pp. 13171-13174.

Nyhus, "Formation of the Porous Structure During the Polymerization of meta-Divinylbenzene and para-Divinylbenzene with Toluene and 2-Ethylhexanoic Acid (2-EHA) as Porogens", Journal of Polymer Science: Part A: Polymer Chemistry, 1999, vol. 37, pp. 3973-3990.

Peng, "Study on biological effect of La3þ on *Escherichia coli* by atomic force microscopy", Journal of Inorganic Biochemistry, 2004, vol. 98, pp. 68-72.

Podlesnyuk, "Sorption of Organic Vapours by Macroporous and Hypercrosslinked Polymeric Adsorbents", Reactive & Functional Polymers, 1999, vol. 42, pp. 181-191.

Rusak, "Complex formation of quercetin with lanthanum enhances binding to plant, Viral satellite double stranded RNA", Journal of Inorganic Biochemistry, 2009, vol. 103, No. 12, pp. 1597-1601.

Stevens, "Bacterial separation and concentration from complex sample matrices", A review. CRC Critical Reviews in Microbiology, 2004, vol. 30, No. 1, pp. 7-24.

Texier, "Selective biosorption of lanthanide (La, Eu, Yb) ions by an immobilized bacterial biomass", Water Sci. and Technology, 2000, vol. 42, pp. 5-6, pp. 91-94.

Zhang, "Lanthanum-based concentration and microrespirometric detection of microbes in water", Water Research, Jun. 1, 2010, vol. 44, No. 11, pp. 3385-3392. XP027057227.

Zhang, "Superhydrophobic nanoporous polymers as efficient adsorbents for organic compounds", Nano Today, 2009, vol. 4, pp. 135-142.

International Search Report for PCT International Application No. PCT/US2013/042359 mailed on Aug. 2, 2013, 4 pages.

* cited by examiner

LANTHANUM-BASED CONCENTRATION AGENTS FOR MICROORGANISMS

CROSS REFERENCE TO RELATED APPLICATIONS

This application is a national stage filing under 35 U.S.C. 371 of PCT/US2013/042359, filed May 23, 2013, which claims priority to Provisional Application No. 61/655,601, filed Jun. 5, 2012, the disclosure of which is incorporated by reference in its/their entirety herein.

FIELD

Concentration agents for microorganisms, articles that include the concentration agents, and processes for concentrating microorganisms are provided.

BACKGROUND

Infections resulting from microorganism contamination are a growing concern. Thus, it is often desirable or necessary to assay for the presence of microorganisms in various clinical, food, environmental, and other types of samples to identify and/or to quantify the microorganisms that are present. The ability to detect the presence of a particular microorganism is often dependent on the concentration of the microorganism in the sample being analyzed.

Various physical concentration methods such as, for example, filtration, chromatography, centrifugation, and gravitational settling have been utilized for non-specific capture of various microorganisms. These physical concentration methods have varied in speed, cost (e.g., at least some of the known methods require expensive equipment, materials, and/or trained technicians), sample requirements (e.g., sample nature and/or volume limitations), space requirements, ease of use (e.g., at least some of the known methods require complicated multi-step processes), suitability for on-site use, effectiveness, or a combination thereof. Inorganic materials such as various metal hydroxides and/or metal oxides have been used as concentration agents for the microorganisms in some of these methods such as those described, for example, in PCT International Publication Numbers WO 2009/046183 A1 (Kshirsagar), WO 2009/046191 A2 (Kshirsagar), WO 2009/085357 A2 (Kshirsagar), WO 2010/114725 A1 (Kshirsagar), WO 2010/114727 A1 (Kshirsagar), and WO 2011/079038 (Kshirsagar).

SUMMARY

New concentration agents suitable for the non-specific concentration of microorganisms (for example, strains of bacteria, fungi, yeasts, protozoan, viruses, and bacterial endospores) are desired and are provided herein. Additionally, articles that include the concentration agent and methods of concentrating a microorganism using the concentration agent are provided. The concentration agent contains both lanthanum and carbonate.

The concentration agents can be used to increase the concentration of microorganism such as pathogenic microorganisms to a level suitable for detection. The concentration agents provide a rapid, inexpensive, and simple (involving no complex equipment or procedures) method of concentrating various microorganisms. The concentration agents can be used effectively under a variety of conditions such as with a variety of sample matrices, a variety of bacterial loads, and a variety of sample volumes.

In a first aspect, a process for concentrating a microorganism is provided. The process includes providing a concentration agent that contains both lanthanum and carbonate. The concentration agent has a weight ratio of carbon to lanthanum that is at least 0.05. The process further includes providing a fluid sample that contains the microorganism and contacting the concentration agent with the fluid sample. The process still further includes binding the microorganism to the concentration agent to form a bound microorganism.

In a second aspect, an article is provided that includes a concentration agent and a microorganism bound to the concentration agent. The concentration agent contains both lanthanum and carbonate. The concentration agent has a weight ratio of carbon to lanthanum that is at least 0.05.

In a third aspect, an article is provided that includes a concentration agent and a porous matrix. The concentration agent contains both lanthanum and carbonate. The concentration agent has a weight ratio of carbon to lanthanum that is at least 0.05. The concentration agent is distributed on a surface of the porous matrix, throughout the porous matrix, or a combination thereof.

DETAILED DESCRIPTION

A concentration agent, articles that include the concentration agent in a porous matrix, and processes of concentrating a microorganism using the concentration agent are provided. More specifically, the concentration agent contains both lanthanum and carbonate. The concentration agent can be used to concentrate or capture microorganisms. The concentration agent is generally not specific to any particular strain, species, or type of microorganism and can therefore be used for the concentration of a general population of microorganisms in a sample. Specific microorganisms can be detected from among the captured microorganism population using any known detection method directed to the specific microorganism.

The terms "a", "an", "the", "at least one" are used interchangeably.

The term "and/or" means one or both of the listed elements. For example, A and/or B means, A alone, B alone, or both A and B.

The term "comprises" and variations thereof do not have a limiting meaning when used in the description and claims.

A numerical range includes the endpoints of the range and all numbers within the range.

The concentration agent contains both lanthanum and carbonate. The concentration agent has a weight ratio of carbon to lanthanum that is at least 0.05, at least 0.06, at least 0.7, at least 0.8, at least 0.9, or at least 0.10. The weight ratio of carbon to lanthanum is often up to 0.20 or higher, up to 0.18, up to 0.16, up to 0.15, up to 0.14, or up to 0.13. The weight ratio of carbon to lanthanum is often in a range of 0.05 to 0.20, in a range of 0.05 to 0.18, in a range of 0.05 to 0.16, in a range of 0.05 to 0.14, in a range of 0.06 to 0.14, or in a range of 0.08 to 0.14.

The carbon in the concentration agent is often from the carbonate included in the concentration agent. The ratio of the moles of lanthanum to the moles of carbonate is typically at least 0.3. This ratio is often at least 0.4, at least 0.5, or at least 0.6. The ratio often is no greater than 5, no greater than 4, no greater than 3, or no greater than 2. For example, the ratio of the moles of lanthanum to the moles of carbonate can be in a range of 0.3 to 5, in a range of 0.4 to 4, in a range of 0.4 to 3, in a range of 0.5 to 3, or in a range of 0.5 to 2.

The lanthanum and carbonate in the concentration agent are often present in the form of various lanthanum/carbonate-containing materials. As used herein the phrase "lanthanum/carbonate-containing material" refers to a material containing both lanthanum and carbonate. The lanthanum/carbonate-containing material can include, for example, lanthanum carbonate, lanthanum oxycarbonate, lanthanum hydroxycarbonate, and the like, and mixtures thereof. Any of these lanthanum/carbonate-containing materials can be present in an anhydrous form, hydrated form, or both. Hydrated forms of lanthanum carbonate are often represented by the formula $La_2(CO_3)_3 \cdot xH_2O$ where x is a number up to 8 such as a number in a range of 2 to 8, in a range of 4 to 8, or in a range of 3 to 6. For example, the hydrated lanthanum carbonate can be $La_2(CO_3)_3 \cdot 4H_2O$ or $La_2(CO_3)_3 \cdot 8H_2O$. The anhydrous form of lanthanum carbonate is typically represented by the formula $La_2(CO_3)_3$. The hydrated forms of lanthanum oxycarbonate are often represented by the formula $La_2O(CO_3)_2 \cdot yH_2O$ or $La_2O_2CO_3 \cdot zH_2O$ where y and z are each independently a number up to 4 such as a number in the range of 1 to 4 or 2 to 4. The anhydrous form of lanthanum oxycarbonate is often represented by the formula $La_2O(CO_3)_2$ or $La_2O_2CO_3$. The anhydrous form of lanthanum hydroxycarbonate is often represented by the formula $La(OH)(CO_3)$.

In some embodiments, the concentration agent does not contain lanthanum oxide. In other embodiments, the concentration agent includes up to 20 weight percent lanthanum oxide. For example, the concentration agent can contain up to 10 weight percent, up to 5 weight percent, up to 2 weight percent, or up to 1 weight percent lanthanum oxide. Even if there is some lanthanum oxide present, the ratio of the moles of lanthanum to the moles of carbonate in the concentration agent is still in a range of 0.3 to 5.

The concentration agent typically includes particles. Stated differently, the lanthanum/carbonate-containing material in the concentration agent is often in the form of a plurality of particles. Although these particles can have any desired size, the average size (i.e., the average size of the largest dimension) of the particles is typically no greater than 100 micrometers, no greater than 75 micrometers, no greater than 50 micrometers, no greater than 40 micrometers, no greater than 30 micrometers, no greater than 20 micrometers, or no greater than 10 micrometers. The particles typically have an average particle diameter that is greater than 1 micrometer, greater than 2 micrometers, or greater than 5 micrometers. For example, the average diameter of the particles can be in a range of 1 to 100 micrometers, 1 to 75 micrometers, 1 to 50 micrometers, 1 to 20 micrometers, or 1 to 10 micrometers.

The particles of the lanthanum/carbonate-containing material can have any shape. In some embodiments, the particles have a platelet-like morphology. That is, one of the three dimensions of the particle (i.e., the x-direction, y-direction, or z-direction) is considerably smaller than the other two dimensions. For example, the z-direction can be less than 20 percent, less than 10 percent, less than 5 percent, less than 2 percent, or less than 1 percent of the other two dimensions. In other embodiments, the particles are nearly spherical. The spherical morphology can result from a single particle or from agglomeration and/or aggregation of individual particles.

In some embodiments, the lanthanum/carbonate-containing material includes crystalline material having a well defined x-ray diffraction pattern. In other embodiments, the lanthanum/carbonate-containing material includes amorphous material with an x-ray diffraction pattern without peaks or with only broad peaks. In yet other embodiments, the lanthanum/carbonate-containing material has an x-ray diffraction pattern suggesting the presence of a disordered crystalline arrangement, small crystalline regions, or both. Such x-ray diffraction patterns can have either only broad peaks or a mixture of sharp and broad peaks.

Any suitable method can be used to prepare the lanthanum/carbonate-containing material. In some embodiments, the lanthanum/carbonate-containing material is prepared by forming a precipitate by the addition of a water-soluble carbonate salt, a water-soluble bicarbonate salt, or a mixture thereof to a water-soluble lanthanum salt. Suitable water-soluble lanthanum salts include, but are not limited to lanthanum chloride, lanthanum nitrate, lanthanum acetate, and the like. Suitable water-soluble carbonate salts and/or bicarbonate salts include, but are not limited to, sodium carbonate, sodium bicarbonate, potassium carbonate, potassium bicarbonate, ammonium carbonate, ammonium bicarbonate, and the like. An equivalent or an excess amount of the carbonate and/or bicarbonate salt is typically added relative to the moles of lanthanum in the reaction mixture.

Both the rate of addition of the carbonate and/or bicarbonate salt to the lanthanum salt and the reaction temperature (for example, from room temperature to 100° C.) can be adjusted to alter the size of the precipitated particles of lanthanum/carbonate-containing material. Typically, a slower rate of addition or a higher reaction temperature tends to result in the formation of larger particles. Additionally, the pH can be adjusted to alter the reaction rate. In general, increasing the pH tends to decrease the reaction rate. The desired pH can be achieved, for example, by the use of a buffer containing a mixture of carbonate and/or bicarbonate and hydroxide ions. Further, holding the reaction mixture at an elevated temperature (for example, greater than 50° C. such as in a range of 50° C. to 100° C.) after addition of all the carbonate and/or bicarbonate can be used to increase the average particle size, to narrow the particle size distribution, or both.

The particles of lanthanum/carbonate-containing material can be collected from the reaction mixture after precipitation by filtration or by any other suitable process. The collected particles are often washed with water to remove any excess carbonate and/or bicarbonate, any remaining counter ions of the lanthanum salt, and any remaining counter ions of the carbonate and/or bicarbonate salt used in the reaction mixture. The collected particles can be dried at room temperature or at an elevated temperature such as at a temperature up to 100° C., up to 125° C., or up to 150° C. The resulting lanthanum/carbonate-containing material is often a hydrated form of lanthanum carbonate but can include other materials such as hydrated lanthanum oxycarbonate, hydrated lanthanum hydroxycarbonate, or a mixture thereof.

The precipitated lanthanum/carbonate-containing material can be further subjected to heat treatment (for example, calcination). For example, the precipitated lanthanum/carbonate-containing material can be heat treated (for example, calcined) at a temperature of at least 150° C., at least 200° C., or at least 250° C. The upper heat treatment temperature is typically selected so that at least a majority of the heat treated material is a lanthanum/carbonate-containing material. That is, the upper heat treatment temperature is selected so that less than 20 weight percent of the heat treated material is lanthanum oxide. Further, the capture efficiency for microorganism tends to decrease for concentration agents that are calcined at temperatures greater than about 500° C. The upper heat treatment temperature is usually no greater than 500° C., no greater than 450° C., or no greater than 400° C. The calcination temperature is typically in a range of 150° C. to 500° C., in a range of 150° C. to 400°

C., in a range of 200° C. to 500° C., in a range of 200° C. to 400° C., in a range of 250° C. to 500° C., in a range of 250° C. to 450° C., in a range of 250° C. to 400° C., in a range of 250° C. to 350° C., or in a range of 275° C. to 325° C. The atmosphere used during heat treatment can be air or an inert gas such as nitrogen, argon, or the like.

Heat treatment can alter the chemical composition of the lanthanum/carbonate-containing material. For example, the heat treatment often converts hydrated lanthanum/carbonate-containing materials to anhydrous materials. Lanthanum carbonate materials can be converted to lanthanum oxycarbonate materials. The resulting heat treated lanthanum/carbonate-containing materials can appear to be less crystalline or more crystalline than the precipitated lanthanum/carbonate-containing materials based on the x-ray diffraction pattern.

The heating treatment can alter the effectiveness of the lanthanum/carbonate-containing material for binding a microorganism. In some embodiments, the maximum efficiency for binding microorganisms can be obtained by heating the precipitated lanthanum/carbonate-containing material at a temperature that is close to 300° C. such as in a range 225° C. to 375° C., in a range 250° C. to 350° C., or in a range of 275° C. to 325° C. The resulting lanthanum/carbonate-containing material, which can be a mixture of different compounds, typically has an x-ray diffraction pattern that contains many broad peaks suggesting the presence of a disordered crystalline structure and/or the presence of small crystalline domains.

In some embodiments, the lanthanum/carbonate-containing material is a mixture of different compounds. The mixture can include, for example, at least two different materials selected from anhydrous forms and/or hydrated forms of lanthanum carbonate, lanthanum oxycarbonate, and lanthanum hydroxide carbonate. Such mixtures of multiple compounds can often be more effective as concentration agents than individual compounds.

Microorganisms can be bound to the concentration agent. Stated differently, the lanthanum/carbonate-containing material in the concentration agent can be used to capture, isolate, remove, separate, or concentrate microorganisms from a fluid sample. Any fluid sample of interest can be used that potentially includes a microorganism. The fluid sample can be a liquid, a dispersion or suspension of solids in a liquid, or a dispersion or suspension of a first liquid in a second liquid. The fluid sample can be used directly, can be concentrated (for example, by centrifugation or evaporation), or can be diluted (for example, by addition of a buffer such as a pH buffer solution) prior to contact with the concentration agent. Samples that are in the form of a solid or a semi-solid can be extracted (for example, by washing or rinsing with a fluid) or can be suspended or dispersed in a fluid. Samples can be taken from surfaces by swabbing and/or rinsing with a fluid. The samples can include, but are not limited to, biological samples, environmental samples, food samples, feed samples, laboratory samples, and industrial samples.

Some specific food samples that can be used either directly or indirectly after treatment with a fluid phase include, but are not limited to, fresh produce, ground meat, dairy products, juices, beverages, and the like. Food samples may also result from inspection of food processing equipment, food handling equipment, food preparation areas, and the like. Some specific biological fluids that can be used either directly or indirectly after treatment with a fluid phase include, but are not limited to, whole bloods or a component of whole blood (for example, plasma, a platelet-enriched blood fraction, a platelet concentrate, and packed red blood cells), cell preparations (for example, dispersed tissue, bone marrow aspirate, and vertebral body bone marrow), cell suspensions, urine, saliva, lung fluid, cerebral fluid, wound exudates, wound biopsy samples, ocular fluid, spinal fluid, and lysed preparations. Environmental samples that can be used either directly or indirectly after treatment with a fluid phase include, but are not limited to, potable water, ground water, soil samples, and industrial waste samples. Still other industrial samples are those associated with various bioprocesses or pharmaceutical formulations.

The fluid sample and the concentration agent are brought into contact. The concentration agent can be added to the fluid sample or the fluid sample can be added to the concentration agent. Any suitable amount of the fluid sample and the concentration agent can be used. The volume of the fluid sample is often dependent on the particular application. When the fluid sample is related to a diagnostic or research application, the volume may be in a microliter range (for example, 1 to 1000 microliters). When the fluid sample is related to food pathogen testing or for potable water testing, the volume may be in the milliliter to liter range (for example, 1 milliliter to 10 liters or more). When the fluid sample is related to an industrial application, the volume may be several hundred liters or more. The amount of the concentration agent needed relative to the volume of the fluid sample can be readily determined by those skilled in the art. In some applications, 1 to 10 milligrams of concentration agent per milliliter of sample can be useful.

In many embodiments, at least a portion of the concentration agent can be suspended or dispersed in the fluid sample. For example, a spatula or dipstick or other article bearing the concentration agent can be immersed into a fluid sample. In other examples, a fluid sample can be poured onto a film bearing the concentration agent or a fluid sample can be added to a tube or well containing the concentration agent. In still other examples, the concentration agent and the fluid sample are combined (using any order of addition) in any of a variety of containers. These containers can optionally be capped, closed, or sealed such as capped test tubes and capped bottles or jars. The containers, if desired, can be sterilized prior to addition of the fluid sample.

Contact between the concentration agent and the fluid sample can be enhanced by mixing (for example, stirring, agitation, shaking, or rocking) such that the concentration agent is exposed to a substantial portion of the fluid sample. For small fluid samples such as those having a volume less than or equal to 1 milliliter, mixing methods such as forming a vortex can be used as described, for example, in U.S. Pat. No. 5,238,812 (Coulter et al.). For larger volumes, such as those ranging from 1 milliliter to 10 liters, mixing can be achieved by gently tumbling the concentration agent and the fluid sample in an "end over end" fashion as described, for example, in U.S. Pat. No. 5,576,185 (Coulter et al.). Contacting can be carried out for any desired time period. For fluid samples having volumes of about 100 milliliters or less, the contact time can be up to 60 minutes, up to 45 minutes, up to 30 minutes, up to 20 minutes, up to 10 minutes, or up to 5 minutes. The contact time for such fluid samples is often at least 5 seconds, at least 10 seconds, at least 15 seconds, at least 30 seconds, or at least 1 minute.

If desired, one or more additives can be added to the mixture of fluid sample and concentration agent. Suitable additives include, but are not limited to, lysis reagents, bioluminescence assay reagents, microbial growth media, buffers (for example, to disperse or extract a solid sample), microbial staining reagents, washing buffers (for example, to wash away unbound material), elution agents (for example, serum albumin), surfactants, and mechanical abrasion/elution agents (for example, glass beads).

While the fluid sample is in contact with the concentration agent, microorganisms present in the fluid sample can become bound to the concentration agent. The bound microorganism (i.e., the microorganism bound to the concentration agent) can be separated from the residual fluid sample. In some embodiments, such separation can be accomplished by relying, at least in part, upon gravitational settling. For example, the bound microorganism can settle over of period of time up to 60 minutes, up to 45 minutes, up to 30 minutes, up to 15 minutes, up to 10 minutes, or up to 5 minutes. In other embodiments, such separation can be accomplished by techniques such as centrifugation. In either of these embodiments, the supernatant can be removed by decanting, siphoning, filtration, or other methods known in the art. The bound microorganism can remain at the bottom of the container or vessel used during the separation step. Alternatively, the bound microorganism can be on filter media.

In other methods of contacting the fluid sample with the concentration agent, the concentration agent is part of a concentration device that also includes a porous matrix. The concentration agent in these concentration devices is in the form of a plurality of particles that are distributed on a surface of the porous matrix, throughout the porous matrix, or a combination thereof. Any suitable porous matrix can be used.

In some embodiments of the concentration device, the porous matrix is polymeric and is formed using sinterable polymeric particles. That is, the concentration device includes (a) a porous matrix of sintered polymeric particles and (b) a plurality of concentration agent particles that contain both lanthanum and carbonate. The concentration agent particles are distributed on a surface of the porous matrix, throughout the porous matrix, or a combination thereof.

To form this concentration device, the sinterable polymeric particles and concentration agent particles are mixed together and heated to a temperature sufficient to soften the polymeric particles. Upon cooling, the softened polymeric materials fuse together to form a porous matrix of sintered polymeric particles. The resulting concentration device is often in the form of a solid or self-supporting porous matrix with the concentration agent embedded within the porous matrix, on a surface of the porous matrix, or both. The concentration device can have a complex pore structure (for example, a tortuous path of pores throughout the porous matrix) and can have good mechanical strength.

Polymers that are capable of being sintered when in particulate form include various thermoplastic polymers. Thermoplastic polymers with relatively high viscosities and relatively low melt flow rates can facilitate particle shape retention during the sintering process. That is, if the particle shape is not retained, a body with low or no porosity can result.

Useful thermoplastic polymers include, but are not limited to, polyolefins (including olefin homopolymers and copolymers, as well as copolymers of olefins and other vinyl monomers), polysulfones, polyethersulfones, polyphenylene sulfide, and the like, and combinations thereof. Representative examples of useful polymers include ethylene vinyl acetate (EVA) polymers, ethylene methyl acrylate (EMA) polymers, polyethylenes (including, for example, low density polyethylene (LDPE), linear low density polyethylene (LLDPE), high density polyethylene (HDPE), and ultra-high molecular weight polyethylene (UHMWPE)), polypropylenes, ethylene-propylene rubbers, ethylene-propylene-diene rubbers, polystyrene, poly(1-butene), poly(2-butene), poly(1-pentene), poly(2-pentene), poly(3-methyl-1-pentene), poly(4-methyl-1-pentene), 1,2-poly-1,3-butadiene, 1,4-poly-1,3-butadiene, polyisoprene, polychloroprene, poly(vinyl acetate), poly(vinylidene chloride), poly(vinylidene fluoride), poly(tetrafluoroethylene), and the like, and combinations thereof.

In some more specific concentration devices, the thermoplastic polymer used to form the polymeric porous matrix includes polyethylene such as ultra-high molecular weight polyethylene (UHMWPE). Examples ultra-high molecular weight polyethylene are those having a weight average molecular weight of at least about 750,000 grams/mole, at least 1,000,000 grams/mole, at least 2,000,000 grams/mole, or at least 3,000,000 grams/mole.

The sinterable polymers can have a wide range of particle sizes depending upon the pore (for example, hole, depression, or, preferably, channel) sizes desired in the sintered, polymeric porous matrix. Finer particles can result in finer pore sizes in the porous matrix. Generally, the polymer particles can be micro-particles having an average size (i.e., diameter of the longest dimension) in a range of 1 to 1000 micrometers. For example, the average particle size can be in a range of 1 to 750 micrometers, in a range of 1 to 500 micrometers, in a range of 1 to 300 micrometers, in a range of 5 to 300 micrometers, in a range of 1 to 200 micrometers, in a range of 5 to 200 micrometers, in a range of 10 to 200 micrometers, in a range of 50 to 200 micrometers, or in a range of 100 to 200 micrometers. The resulting pores can be in the micrometer range or less. If desired, the porosity of the porous matrix can also be varied or controlled by using blends of higher and lower melt flow rate thermoplastic polymers.

The thermoplastic polymer particles and the concentration agent particles (and any optional additives, such as wetting agents or surfactants) can be combined and mechanically blended (for example, using commercial mixing equipment) to form a mixture. The mixture is typically blended until it is homogeneous. Generally, the particulate concentration agent can be present in the mixture at a concentration of up to 90 weight percent based on a total weight of solids in the mixture. The solids typically include the polymeric particles, the concentration agent particles, and any additional solids associated with optional additives. If higher amounts of the concentration agent are used, the concentration device may contain an insufficient amount of polymeric material to form a porous matrix and the resulting structure may lack integrity. The concentration agent can be present, for example, in an amount up to 85 weight percent, up to 80 weight percent, up to 75 weight percent, or up to 70 weight percent based on the total weight of solids in the mixture. The amount of the concentration agent is typically at least 5 weight percent based on a total weight of solids in the mixture. If the amount of the concentration agent is lower, the capture efficiency of microorganisms by the concentration agent may be insufficiently low. The amount of the concentration agent is often at least 10 weight percent, at least 20 weight percent, at least 30 weight percent, at least 40 weight percent, or at least 50 weight percent based on the total weight of the solids in the mixture.

Some example concentration devices contain 5 to 90 weight percent concentration agent particles and 10 to 95 weight percent polymeric particles based on the total weight of solids in the mixture. For example, the concentration devices can contain 10 to 80 weight percent concentration agent particles and 20 to 90 weight percent polymeric particles, 20 to 80 weight percent concentration agent particles and 20 to 80 weight percent polymeric particles, 40 to 80 weight percent concentration agent particles and 20 to 60 weight percent polymeric particles, or 10 to 50 weight percent concentration agent particles and 50 to 90 weight percent polymeric particles. Conventional additives (for example, wetting agents, surfactants, or the like) can be included in the mixture in small amounts (for example, up to 5 weight percent), if desired.

The resulting mixture can be placed in a mold or other suitable container or substrate. Useful molds, which can have a single cavity or multiple cavities, can be fabricated from carbon steel, stainless steel, brass, aluminum, titanium, nickel, or the like. The cavities can be of essentially any desired shape, provided that the sintered, polymeric porous matrix can be removed from the mold after processing is completed. The molds can be filed using commercial powder handling and/or vibratory equipment.

Thermal processing to sinter the polymeric particles can be carried out by introducing heat to the mold (for example, through electrical resistance heating, electrical induction heating, or steam heating). The mold can be heated to a temperature sufficient to sinter the polymer (for example, by heating to a temperature slightly below the melting point of the polymer). The temperature is often in a range of 90° C. to 200° C. or higher depending on the molecular weight of the polymeric particles. For example, the temperature can be in a range of 100° C. to 200° C., in a range of 120° C. to 200° C., in a range of 100° C. to 180° C., or in a range of 120° C. to 180° C. Optionally, pressure can be applied to the mixture during the heating process. After thermal processing, the mold can be allowed to cool to ambient temperature (for example, a temperature in a range of 20° C. to 25° C.) naturally or through use of essentially any convenient cooling method or device.

An example concentration device can be prepared using the polymer particles and processing methods described in U.S. Pat. No. 7,112,272 (Hughes et al.), U.S. Pat. No. 7,112,280 (Hughes et al.), and U.S. Pat. No. 7,169,304 (Hughes et al.). Two different types of ultra-high molecular weight polyethylene (UHMWPE) particles can be blended together, one being "popcorn-shaped" with surface convolutions and the other being substantially spherical. Example "popcorn-shaped" and spherical UHMWPEs are available from Ticona (a division of Celanese, headquartered in Frankfurt, Germany) as PMX CF-1 (having a bulk density of 0.25-0.30 grams/cubic centimeter and an average diameter of about 30 to 40 micrometers, with a range from about 10 micrometers to about 100 micrometers) and PMX CF-2 (having a bulk density of 0.40-0.48 grams/cubic centimeter and an average diameter of about 55 to 65 micrometers, with a range from about 10 micrometers to about 180 micrometers), respectively. UHMWPE particles from other manufacturers having comparable morphologies, bulk densities, and particle sizes and having weight average molecular weights in the range of about 750,000 grams/mole to about 3,000,000 grams/mole can also be utilized. The two types of UHMWPE particles can be selected to be of the same or different molecular weight. In one more particular example, both types of particles have a similar molecular weight within the stated range; for example, both types of particles can have a weight average molecular weight close to 3,000,000 grams/mole). The two types of UHMWPE particles can be combined in varying relative amounts (for example, equal amounts) and then further combined with concentration agent in the ratios described above. Either type of UHMWPE can be used in lesser amount than the other, or can even be omitted from the mixture, depending upon the desired characteristics of the concentration device.

In other embodiments of a concentration device, the porous matrix is fibrous and nonwoven. That is, the concentration device includes (a) a fibrous, nonwoven porous matrix and (b) a plurality of concentration agent particles that contain both lanthanum and carbonate. The concentration agent particles are distributed on a surface of the porous matrix, throughout the porous matrix, or a combination thereof.

Such concentration devices can be prepared by essentially any process that is capable of providing a fibrous nonwoven porous matrix having the concentration agent particles enmeshed therein. This type of porous matrix is typically a web or medium that contains interlaid fibers in a form that is not woven or knitted fabric. Useful processes for preparing the fibrous, nonwoven porous matrix include, but are not limited to, air laying techniques, spunlaid techniques such as meltblowing or spunbonding, carding, wetlaying, and combinations thereof. In some applications, it may be preferable to prepare the fibrous nonwoven matrix by spunlaid or wetlaid techniques.

Fibers suitable for use in preparing the fibrous, nonwoven porous matrix of the concentration device are usually pulpable or extrudable fibers such as those that are stable to radiation and/or to a variety of solvents. Useful fibers include polymeric fibers, inorganic fibers, and combinations thereof. In many embodiments, the fibers include polymeric fibers and often include a plurality of different types of polymeric fibers. For example, at least some of the polymeric fibers can be selected to exhibit a degree of hydrophilicity.

Suitable polymeric fibers include those made from natural polymers (those derived from animal or vegetable sources) and/or synthetic polymers, including thermoplastic and solvent-dispersible polymers. Useful polymers include wool; silk; cellulosic polymers (for example, cellulose, cellulose derivatives such as rayon, and the like); fluorinated polymers (for example, poly(vinyl fluoride), poly(vinylidene fluoride), copolymers of vinylidene fluoride such as poly(vinylidene fluoride-co-hexafluoropropylene), copolymers of chlorotrifluoroethylene such as poly(ethylene-co-chlorotrifluoroethylene), and the like); chlorinated polymers; polyolefins (for example, poly(ethylene), poly(propylene), poly (1-butene), copolymers of ethylene and propylene, alpha olefin copolymers such as copolymers of ethylene or propylene with 1-butene, 1-hexene, 1-octene, and 1-decene, poly(ethylene-co-1-butene), poly(ethylene-co-1-butene-co-1-hexene), and the like); poly(isoprenes); poly(butadienes); polyamides (for example, nylon 6, nylon 6,6, nylon 6,12, poly(iminoadipoyliminohexamethylene), poly(iminoadipoyliminodecamethylene), polycaprolactam, and the like); polyimides (for example, poly(pyromellitimide) and the like); polyethers; poly(ether sulfones) (for example, poly (diphenylether sulfone), poly(diphenylsulfone-co-diphenylene oxide sulfone), and the like); poly(sulfones); poly (vinyl acetates); copolymers of vinyl acetate (for example, poly(ethylene-co-vinyl acetate), copolymers in which at least some of the acetate groups have been hydrolyzed to provide various poly(vinyl alcohols) including poly(ethylene-co-vinyl alcohol), and the like); poly(phosphazenes); poly(vinyl esters); poly(vinyl ethers); poly(vinyl alcohols); polyaramids (for example, para-aramids such as poly(paraphenylene terephthalamide) and fibers sold under the trade designation "KEVLAR" by DuPont Co., Wilmington, Del., pulps of which are commercially available in various grades based on the length of the fibers that make up the pulp such as, for example, "KEVLAR 1F306" and "KEVLAR 1F694", both of which include aramid fibers that are at least 4 mm in length; and the like); poly(carbonates); and the like; and combinations thereof. In some specific examples, the polymeric fibers include polyamides, polyolefins, polysulfones, and combinations thereof. An even more specific example includes nylon, poly(ethylene), and combinations thereof.

Suitable inorganic fibers include those that contain at least one inorganic material selected from glasses, ceramics, and combinations thereof. Useful inorganic fibers include, for example, fiberglass (for example, E-glass, S-glass, and the like), ceramic fibers (for example, fibers made of metal oxides (such as alumina), silicon carbide, boron nitride, boron carbide, and the like), and combinations thereof. Useful ceramic fibers can be at least partially crystalline (exhibiting a discernible X-ray powder diffraction pattern or containing both crystalline and amorphous (glass) phases). In some applications, the inorganic fibers include fiberglass and combinations thereof.

The fibers used to form the fibrous nonwoven porous matrix can be of a length and diameter that can provide a porous matrix having sufficient structural integrity and sufficient porosity for a particular application (for example, for a particular type of sample matrix). For example, the fiber lengths are often at least about 0.5 millimeter, at least 1 millimeter, at least 2 millimeters, at least 3 millimeters, at least 4 millimeters, at least 6 millimeters, at least 8 millimeters, at least 10 millimeters, at least 15 millimeters, at least 20 millimeters, at least 25 millimeters, or at least 30 millimeters. The diameter of the fibers can be, for example, at least 10 micrometers, at least 20 micrometers, at least 40 micrometers, or at least 60 micrometers. The fiber lengths and diameters will vary depending upon factors such as the nature of the fiber and the type of application.

To facilitate entrapment of the concentration agent particles and/or to ensure a high surface area, the fibers used to form the fibrous nonwoven porous matrix often contain at least one fibrillated fiber (for example, in the form of a main fiber surrounded by many smaller attached fibrils). The main fiber generally can have a length in the range of 0.5 millimeters to 5 millimeters and a diameter in a range of 1 micrometer to 20 micrometers. The fibrils typically can have a sub-micrometer diameter.

The fibrous nonwoven porous matrix can contain a plurality of different types of fibers. In some embodiments, the porous matrix can be formed using two, three, four, or even more different types of fibers For example, a nylon fiber can be added for strength and integrity, while fibrillated polyethylene can be added for entrapment of the particulates. If fibrillated and non-fibrillated fibers are used in combination, the weight ratio of fibrillated fibers to non-fibrillated fibers is often at least 1:2, at least 1:1, at least 2:1, at least 3:1, at least 5:1, or even at least 8:1.

The concentration devices often contain at least 10 weight percent fibers based on a total weight of solids in the concentration device (for example, fiber, polymeric binder, and concentration agent). If the amount of fibers included is less than this amount, the concentration device may not have sufficient porosity. Some concentration devices contain at least 15 weight percent, at least 20 weight percent, or at least 25 weight percent fibers. The fibrous porous matrix often contains up to 95 weight percent fibers based on a total weight of solids. If the amount of fiber is greater than this amount, there may be an insufficient amount of the concentration agent present to capture microorganisms when contacted with a fluid sample. Some example concentration devices contain up to 90 weight percent, up to 80 weight percent, up to 70 weight percent, up to 60 weight percent, or up to 50 weight percent fibers based on the total weight of solids.

The fibrous, nonwoven porous matrix often further contains at least one polymeric binder. Suitable polymeric binders include natural and synthetic polymeric materials that are relatively inert (exhibiting little or no chemical interaction with either the fibers or the concentration agent particles). Useful polymeric binders include polymeric resins (for example, in the form of powders and latexes), polymeric binder fibers, and the like, and combinations thereof.

Suitable polymeric resins for used in the fibrous, nonwoven porous matrix include, but are not limited to, natural rubbers, neoprene, styrene-butadiene copolymers, acrylate resins, polyvinyl chloride, polyvinyl acetate, and combinations thereof. In many embodiments, the polymeric resin includes acrylate resins.

Suitable polymeric binder fibers include adhesive-only type fibers and bi-component fibers. Example adhesive-only type fibers include those commercially available under the trade designation KODEL (for example, KODEL 43UD) from Eastman Chemical Products (Kingsport, Tenn., USA). Bi-component fibers can be, for example, side-by-side forms, sheath-core forms, or the like. An example side-by-side bi-component fiber is the polyolefin thermally bonded bi-component fiber that is commercially available from Chisso Corporation (Osaka, Japan) under the trade designation CHISSO (for example, CHISSO ES). An example sheath-core bi-component fiber is commercially available from Unitika Ltd. (Osaka, Japan) under the trade designation MELTY (for example, MELTY 4080) and Minifibers (Johnson City, Tenn.) made of ethyl vinyl acetate (sheath) and polypropylene (core). This fiber has a polyester core and a poly(ethylene) sheath.

Regardless of the type of polymeric binder used, the amount of binder in the resulting concentration device (in dry form) is often in a range of 0.5 to 10 weight percent based on a total weight of solids in the concentration device (for example, fiber, polymeric binder, and concentration agent). Such amounts of polymeric binder generally can provide the fibrous, nonwoven porous matrix with sufficient integrity for use in many applications, while not significantly coating the concentration agent particles. For example, the amount of polymeric binder can be in a range of 1 to 8 weight percent, 1 to 6 weight percent, 1 to 5 weight percent, 1 to 4 weight percent, 2 to 8 weight percent, or 3 to 7 weight percent based on a total weight of solids in the concentration device.

Preferably, the polymeric binder does not substantially adhere to the concentration agent particles. In other words, when the concentration device is examined by scanning electron microscopy, less than 5 percent of a total surface area of the concentration agent particle is covered with polymeric binder. For example, less than 4 percent, less than 3 percent, less than 2 percent, or even less than 1 percent of the total surface area of the concentration agent is covered with the polymeric binder.

This type of concentration device can be prepared by a process that includes (a) providing a plurality of the above-described fibers; (b) providing a plurality of the above-described concentration agent particles; and (c) forming at least a portion of the plurality of fibers into a porous fibrous nonwoven matrix having at least a portion of the plurality of concentration agent particles enmeshed therein. As mentioned above, the forming can be carried out by essentially any process that is capable of providing a fibrous nonwoven matrix having the concentration agent particles enmeshed therein.

One more specific process for preparing the concentration device is a wet laying or "wetlaid" process. In this process, a dispersion is formed that contains (a) a plurality of fibers, (b) a plurality of concentration agent particles, (c) a polymeric binder, (d) and a dispersing liquid such as water, a water-miscible organic solvent, or a mixture thereof. The fibers, concentration agent particles, and polymeric binder components can be dispersed together in the dispersing liquid. Alternatively, one or two of these components can be dispersed prior to the introduction of the other components. In some embodiments, the fibers have additives, surface treatments, or chemical groups that facilitate dispersion of the fibers in the dispersion liquid. For example, polyolefin-based fibers can have maleic anhydride or succinic anhydride functionality, or, during the melt-processing to prepare polyolefin-based fibers, a suitable surfactant can be added.

The wetlaid process additionally includes at least partially depositing the polymeric binder onto at least a portion of the fibers and removing the dispersing liquid from the dispersion. Deposition of the polymeric binder onto the fibers can be carried out either before or after the dispersing liquid removal or dewatering step, depending upon the nature of the polymeric binder. For example, when polymeric latex is used as the polymeric binder, the polymeric latex can be precipitated onto the fibers before or after concentration agent particle addition and prior to dewatering. After the initial dewatering, heat can be applied to finish the dewatering and to set the resulting deposited latex. When polymeric binder fibers are used as the polymeric binder, dewatering can generally be carried out first, followed by heating to finish the dewatering and to melt the polymeric binder fibers (and thereby deposit polymeric binder on the fibers).

One or more adjuvants or additives can be used in preparing this type of concentration device. Useful adjuvants include process aids (for example, precipitation agents such as sodium aluminates and aluminum sulfate, which can aid in precipitating the polymeric binder onto the fibers), materials that can enhance the overall performance of the resulting concentration device, and the like. When used, the amounts of such adjuvants can be present, for example, in an amount up 5 weight percent, up to 4 weight percent, up to 3 weight percent, up to 1 weight percent, or up to 0.5 weight percent based on a total dry weight of the concentration device (for example, fibers, concentration agent, and polymeric binder). The total amount of adjuvants is typically selected to be as low as possible so as to maximize the amount of concentration agent particles that can be included in the concentration device.

In one more specific wetlaid process, the fibers (for example, chopped fibers) can be blended in a container in the presence of the dispersing liquid (for example, water, a water-miscible organic solvent such as an alcohol, or a mixture thereof) to form a slurry. After formation of the slurry, the concentration agent particles, the polymeric binder, and an optional precipitation agent (for example, a pH adjusting agent such as alum) can be added to the slurry.

When the wetlaid process is carried out by using hand-sheet methods known in the art, the order of addition of the three components (i.e., fibers, polymeric binder, and concentration agent particles) to the dispersion has not been found to significantly affect the ultimate performance of the concentration device. Addition of the polymeric binder after addition of the concentration agent particles, however, can provide a concentration device exhibiting somewhat greater adhesion of the concentration agent particles to the fibers.

After formation, the dispersion mixture can be poured into a mold, the bottom of which can be covered by a screen. The dispersing liquid can be allowed to drain from the mixture (in the form of a wet sheet) through the screen. After sufficient liquid has drained, the wet sheet generally can be removed from the mold and dried by pressing, heating, or a combination of the two. Generally pressures are in a range of about 300 to about 600 kPa. Temperatures in a range of 90° C. to 200° C., in a range of 100° C. to 175° C., in a range of 100° C. to 150° C., or in a range of 90° C. to 120° C. can be used for drying the wet sheet. Drying often removes all or most of the dispersing liquid (for example, up to 85 weight percent, up to 90 weight percent, up to 95 weight percent, up to 98 weight percent, or up to 99 weight percent of the dispersing liquid based on the amount of dispersing liquid added to form the dispersion). When polymeric binder fibers are used as the polymeric binder in the wetlaid process, a precipitation agent is typically not needed and the applied heat can be used to melt the polymeric binder fibers.

The resulting dry sheet can have an average thickness of at least 0.1 millimeter, at least 0.2 millimeters, at least 0.5 millimeters, at least 0.8 millimeters, at least 1 millimeter, at least 2 millimeters, at least 4 millimeters, or at least 5 millimeters. The average thickness is often up to 20 millimeters, up to 15 millimeters, up to 12 millimeters, or up to 10 millimeters. Calendering can be used to provide additional pressing or fusing, if desired, of the dry sheet.

In the concentration devices that include a fibrous, nonwoven porous matrix, the concentration agents can be entrapped through either chemical interactions (for example, chemical bonding) or physical interactions (for example, adsorption or mechanical entrapment), depending upon the nature of the fibers that are utilized.

Since the capacity and efficiency of the concentration device can vary according to the amount of concentration agent particles contained therein, relatively high particle loadings generally can be desirable. The amount of the concentration agent in the concentration device is often in a range of 5 to 90 weight percent based on a total weight of solids in the concentration device (for example, fibers, polymeric binder, and concentration agent). If less than 5 weight percent of the concentration agent is used, the effectiveness of the concentration device for concentrating microorganisms may be undesirably low. If more than 90 weight percent of the concentration agent is used, there may be too few fibers present to form a porous matrix or the structure may lack integrity. In some example concentration devices, the concentration agent is present in an amount equal to at least 10 weight percent, at least 20 weight percent, at least 30 weight percent, at least 40 weight percent, or at least 50 weight percent based on the total weight of solids in the concentration device. The amount of concentration agent particles in the concentration device is often up to 85 weight percent, up to 80 weight percent, up to 75 weight percent, up to 70 weight percent, or up to 60 weight percent based on the total weight of solids in the concentration device. The concentration agents are often preferably distributed essentially uniformly throughout the porous matrix.

Generally the average pore size of the dry sheet material can be in a range of 0.1 to 10 micrometers, as measured by scanning electron microscopy (SEM). Void volumes in the range of 20 to 80 volume percent or in a range of 40 to 60 volume percent can be useful. The porosity of the dry sheet materials can be modified (increased) by using fibers of larger diameter or stiffness in the fiber mixture.

The dry sheet material can be flexible (for example, it can be rolled around a 0.75 inch (about 2 cm) diameter core). This flexibility can enable the sheet material to be pleated or rolled. The sheet material can have a relatively low back pressure (i.e., a relatively high volume of liquid can be relatively quickly passed through it without generating a relatively high back pressure). As used herein, "relatively low back pressure" refers to a differential back pressure no greater than 3 pounds per square inch (20.7 kPa), no greater than 2.5 pounds per square inch (17.2 kPa), no greater than 2 pounds per square inch (13.8 kPa), no greater than 1.5 pounds per square inch (10.3 kPa), no greater than 1 pound per square inch (6.9 kPa), or no greater than 0.5 pounds per square inch (3.5 kPa) at a 3 mL/cm$^2$ flowrate, wherein the flowrate is based on the frontal surface area of the sheet material.

The uncalendered sheet material can be cut to a desired size and used to bind a microorganism when contacted with a fluid sample. If desired (for example, when a significant pressure drop across the sheet is not a concern), the sheet material can be calendered to increase its tensile strength prior to use. When the sheet material is to be pleated, drying and calendering are typically avoided.

In some concentration devices with a fibrous, nonwoven porous matrix, a single layer of the dry sheet material can be effective. In other concentration devices, multiple layers of the dry sheet material are used to provide greater binding capacity for microorganisms.

Any of the above described concentration devices can further include one or more other components such as, for example, one or more pre-filters (for example, to remove relatively large particles from a sample prior to passage through the porous matrix), a manifold for applying a pressure differential across the device (for example, to aid in passing a sample through the porous matrix), and/or an external housing (for example, a disposable cartridge to contain and/or protect the porous matrix).

Any of the above described concentration devices can be contacted with a fluid sample containing a microorganism in any suitable manner. The concentration device can be added to the fluid sample, or the fluid sample can be added to the concentration device. The concentration device can be immersed in a fluid sample, a fluid sample can be poured onto the concentration device, a fluid sample can be poured into a tube or well containing the concentration device, or a sample can be passed over or through the concentration device. Preferably, the contacting is carried out in a manner such that the fluid sample passes through at least one pore of the porous matrix.

The concentration device and the fluid sample can be combined (using any order of addition) in any of a variety of containers or holders. Suitable containers or holders are typically designed to hold both the concentration device and the fluid sample without leakage. Some example containers can be capped, closed, or sealed. In some embodiments, the container or holder is a column or a syringe barrel. Suitable containers for use in carrying out the process of the invention will be determined by the particular sample and can vary widely in size and nature. For example, the container can be small, such as a 10 microliter container (for example, a test tube or syringe) or larger, such as a 100 milliliter to 3 liter container (for example, an Erlenmeyer flask or an annular cylindrical container).

The container, the concentration device, and any other apparatus or additives that contact the fluid sample directly can be sterilized (for example, by controlled heat, ethylene oxide gas, or radiation) prior to use, in order to reduce or prevent any contamination of the fluid sample that might cause detection errors. The amount of concentration agent in the concentration device that is sufficient to capture or concentrate the microorganisms of a particular fluid sample for successful detection will vary (depending upon, for example, the nature and form of the concentration agent and device and the volume of the fluid sample) and can be readily determined by one skilled in the art.

The period of contact between the concentration device and the fluid sample can be any desired amount of time. For example, the contact time can be up to 24 hours, up to 12 hours, up to 6 hours, up to 4 hours, up to 2 hours, up to 1 hour, up to 30 minutes, up to 15 minutes, up to 10 minutes, up to 5 minutes, up to 1 minute, up to 30 seconds, or up to 15 seconds. Contact can be enhanced by mixing (for example, by stirring, by shaking, or by application of a pressure differential across the concentration device to facilitate passage of fluid a sample through its porous matrix).

In some embodiments, the fluid sample is passed at least once (often, only once) through the concentration device (for example, by pumping, pressure, or gravity feed). Essentially any type of pump (for example, a peristaltic pump) or other equipment for establishing a pressure differential across the concentration device (for example, a syringe or plunger) can be utilized. Sample flow rates through the concentration device of up to about 100 milliliters per minute or more can be effective. The flow rates can be, for example, in a range of 1 to 100 milliliters per minute, in a range of 10 to 100 milliliters/minute, in a range of 10 to 50 milliliters per minute, or in a range of 10 to 25 milliliters per minute.

If desired, one or more optional additives can be added to the mixture of fluid sample and concentration device. Suitable additives include, but are not limited to, lysis reagents, bioluminescence assay reagents, microbial growth media, buffers (for example, to disperse or extract a solid sample), microbial staining reagents, washing buffers (for example, to wash away unbound material), elution agents (for example, serum albumin), surfactants, and mechanical abrasion/elution agents (for example, glass beads).

While the fluid sample is in contact with the concentration device, microorganisms present in the fluid sample can become bound to the concentration agent in the concentration device. The bound microorganism (i.e., the microorganisms bound to the concentration agent in the concentration device) is typically separated from the residual fluid sample. It can also be possible to isolate or separate bound microorganisms (or one or more components thereof) from the concentration device after contacting. For example, an elution agent or a lysis agent can be passed over or through the concentration device.

Any of the above described concentration devices can be used as a filter media for removing microbial contaminants or pathogens from a fluid sample (for example, water). The filter media include a porous matrix and a plurality of concentration agent particles distributed on a surface of the porous matrix, distributed throughout the porous matrix, or a combination thereof. In some embodiments, the filter media contains (a) a fibrous, nonwoven porous matrix and (b) a plurality of concentration agent particles, the particles enmeshed in the porous fibrous nonwoven matrix. In other embodiments, the filter media contains (a) a porous matrix of sintered polymeric particles and (b) a plurality of concentration agent particles, the particles embedded in the porous matrix of sintered polymeric particles.

A variety of microorganisms can be concentrated and detected by using the above described concentration agents and concentration devices. Samples can contain a plurality of microorganism strains, and any one strain can be detected independently of any other strain. These microorganisms include, but are not limited to, bacteria (including gram-positive bacteria and gram-negative bacteria), fungi, molds, yeasts, protozoans, viruses (including both non-enveloped and enveloped viruses), bacterial endospores, and the like, and combinations thereof.

Genera of target microorganisms to be detected include, but are not limited to, *Listeria, Escherichia, Salmonella, Campylobacter, Clostridium, Helicobacter, Mycobacterium, Staphylococcus, Shigella, Enterococcus, Bacillus, Neisseria, Shigella, Streptococcus, Vibrio, Yersinia, Bordetella, Borrelia, Pseudomonas, Saccharomyces, Candida*, and the like, and combinations thereof.

Specific microorganism strains that can be targets for detection include *Escherichia coli, Yersinia enterocolitica, Yersinia pseudotuberculosis, Vibrio cholerae, Vibrio parahaemolyticus, Vibrio vulnificus, Listeria monocytogenes, Staphylococcus aureus, Salmonella enterica, Saccharomyces cerevisiae, Candida albicans, Staphylococcal enterotoxin* ssp, *Bacillus cereus, Bacillus anthracia, Bacillus atrophaeus, Bacillus subtilis, Clostridium perfringens, Clostridium botulinum, Clostridium difficile, Enterobacter sakazakii, Pseudomonas aeruginosa*, and the like, and combinations thereof.

The microorganisms typically remain viable even after being bound to the concentration agent. They are capable of replicating or reproducing upon availability of favorable conditions such as suitable nutrients.

The capture efficiency, which can also be referred to as the binding efficiency of the concentration agent for microorganisms, is typically at least 50 percent, least 60 percent, at least 70 percent, at least 80 percent, at least 90 percent, or at least 95 percent based on the total amount of microorganisms in a sample.

Microorganisms that have been captured or bound (for example, by adsorption or by sieving) by the concentration device or concentration agent can be detected by essentially any desired method that is currently known or hereafter developed. Such methods include, for example, culture-based methods (which can be preferred when time permits), microscopy (for example, using a transmitted light microscope or an epifluorescence microscope, which can be used for visualizing microorganisms tagged with fluorescent dyes) and other imaging methods, immunological detection methods, and genetic detection methods. The detection process following microorganism capture optionally can include washing to remove sample matrix components, slicing or otherwise breaking up the porous fibrous nonwoven matrix of the concentration device, staining, boiling or using elution buffers or lysis agents to release cellular analyte from the concentration device, or the like.

Immunological detection is detection of an antigenic material derived from a target organism, which is commonly a biological molecule (for example, a protein or proteoglycan) acting as a marker on the surface of bacteria or viral particles. Detection of the antigenic material typically can be by an antibody, a polypeptide selected from a process such as phage display, or an aptamer from a screening process.

Immunological detection methods are well-known and include, for example, immunoprecipitation and enzyme-linked immunosorbent assay (ELISA). Antibody binding can be detected in a variety of ways (for example, by labeling either a primary or a secondary antibody with a fluorescent dye, with a quantum dot, or with an enzyme that can produce chemiluminescence or a colored substrate, and using either a plate reader or a lateral flow device).

Detection can also be carried out by genetic assay (for example, by nucleic acid hybridization or primer directed amplification), which is often a preferred method. The captured or bound microorganisms can be lysed to render their genetic material available for assay. Lysis methods are well-known and include, for example, treatments such as sonication, osmotic shock, high temperature treatment (for example, from about 50° C. to about 100° C.), and incubation with an enzyme such as lysozyme, glucolase, zymolose, lyticase, proteinase K, proteinase E, or viral enolysins.

Many commonly-used genetic detection assays detect the nucleic acids of a specific microorganism, including the DNA and/or RNA. The stringency of conditions used in a genetic detection method correlates with the level of variation in nucleic acid sequence that is detected. Highly stringent conditions of salt concentration and temperature can limit the detection to the exact nucleic acid sequence of the target. Thus microorganism strains with small variations in a target nucleic acid sequence can be distinguished using a highly stringent genetic assay. Genetic detection can be based on nucleic acid hybridization where a single-stranded nucleic acid probe is hybridized to the denatured nucleic acids of the microorganism such that a double-stranded nucleic acid is produced, including the probe strand. One skilled in the art will be familiar with probe labels, such as radioactive, fluorescent, and chemiluminescent labels, for detecting the hybrid following gel electrophoresis, capillary electrophoresis, or other separation method.

Particularly useful genetic detection methods are based on primer directed nucleic acid amplification. Primer directed nucleic acid amplification methods include, for example, thermal cycling methods (for example, polymerase chain reaction (PCR), reverse transcriptase polymerase chain reaction (RT-PCR), and ligase chain reaction (LCR)), as well as isothermal methods and strand displacement amplification (SDA) (and combinations thereof; preferably, PCR or RT-PCR). Methods for detection of the amplified product are not limited and include, for example, gel electrophoresis separation and ethidium bromide staining, as well as detection of an incorporated fluorescent label or radio label in the product. Methods that do not require a separation step prior to detection of the amplified product can also be used (for example, real-time PCR or homogeneous detection).

Bioluminescence detection methods are well-known and include, for example, adensosine triphosphate (ATP) detection methods including those described in U.S. Pat. No. 7,422,868 (Fan et al.). Other luminescence-based detection methods can also be utilized.

Since the concentration agents and concentration devices described above are non-specific or non-strain specific, they can be used to provide a general capture system that allows for multiple microorganism strains to be targeted for assay in the same sample. For example, in assaying for contamination of food samples, it can be desired to test for *Listeria monocytogenes, Escherichia coli*, and *Salmonella* all in the same sample. A single capture step can then be followed by, for example, PCR or RT-PCR assays using specific primers to amplify different nucleic acid sequences from each of these microorganism strains. Thus, the need for separate sample handling and preparation procedures for each strain can be avoided.

A diagnostic kit can be provided that includes (a) at least one above-described concentration device or concentration agent; and (b) at least one testing container or testing reagent (preferably, a sterile testing container or testing reagent) for use in carrying out the concentration process of the invention. Preferably, the diagnostic kit further comprises instructions for carrying out the process.

Useful testing containers or holders include those described above and can be used, for example, for contacting, for incubation, for collection of eluate, or for other desired process steps. Useful testing reagents include microorganism culture or growth media, lysis agents, elution agents, buffers, luminescence detection assay components (for example, luminometer, lysis reagents, luciferase enzyme, enzyme substrate, reaction buffers, and the like), genetic detection assay components, and the like, and combinations thereof. A preferred lysis agent is a lytic enzyme or chemical supplied in a buffer, and preferred genetic detection assay components include one or more primers specific for a target microorganism. The kit can optionally further include sterile forceps or the like.

Various items are provided that are processes for concentrating a microorganism or articles that include a concentration agent for microorganisms.

Item 1 is a process for concentrating a microorganism. The process includes providing a concentration agent that contains both lanthanum and carbonate. The concentration agent has a weight ratio of carbon to lanthanum that is at least 0.05. The process further includes providing a fluid sample that contains the microorganism and contacting the concentration agent with the fluid sample. The process still further includes binding the microorganism to the concentration agent to form a bound microorganism.

Item 2 is the process of item 1, wherein the concentration agent comprises particles.

Item 3 is the process of item 2, wherein the particles have an average diameter no greater than 100 micrometers.

Item 4 is the process of any of items 1 to 3, wherein the microorganism is a strain of bacteria, fungi, yeast, protozoan, virus, bacterial endospore, or a mixture thereof.

Item 5 is the process of item 1 to 4, wherein the microorganism is gram-negative bacteria or gram-positive bacteria.

Item 6 is the process of any one of items 1 to 5, wherein the bound microorganism is in a viable state.

Item 7 is the process of any one of items 1 to 6, further comprising segregating the bound microorganism from the fluid sample.

Item 8 is the process of any of items 1 to 7, wherein the concentration agent comprises a plurality of particles and further comprises a porous matrix, wherein the plurality of particles are distributed on a surface of the porous matrix, distributed throughout the porous matrix, or distributed both on the surface and throughout the porous matrix.

Item 9 is the process of item 8, wherein the porous matrix comprises nonwoven fibers.

Item 10 is the process of item 9, wherein the nonwoven fibers comprise fibrillated fibers.

Item 11 is the process of item 9, wherein the nonwoven fibers are polymeric fibers, inorganic fibers, or a combination thereof.

Item 12 is the process of any one of items 9 to 11, wherein the porous matrix further comprises a polymeric binder.

Item 13 is the process of item 8, wherein the porous matrix comprises a sintered polymeric material.

Item 14 is the process of item 13, sintered polymeric material is a sintered thermoplastic polymer.

Item 15 is the process of any one of items 1 to 14, wherein providing the concentration agent comprises forming a precipitate by mixing a water soluble lanthanum salt with a water soluble carbonate solution, with a water soluble bicarbonate solution, or with a mixture thereof.

Item 16 is the process of item 15, wherein providing the concentration agent further comprises heating the precipitate at a temperature in a range of 150° C. to 500° C.

Item 17 is the process of any one of items 1 to 14, wherein providing the concentration agent comprises heating lanthanum carbonate hydrate particles to temperature sufficient to at least partially form anhydrous lanthanum carbonate.

Item 18 is the process of any one of items 1 to 14, wherein the concentration agent comprises lanthanum carbonate, lanthanum oxycarbonate, lanthanum hydroxycarbonate, or a mixture thereof.

Item 19 is the process of item 18, wherein the concentration agent comprises lanthanum carbonate that is anhydrous or hydrated.

Item 20 is the process of item 18, wherein the concentration agent comprises lanthanum oxycarbonate that is anhydrous or hydrated.

Item 21 is the process of any one of items 1 to 20, further comprising detecting the presence of the bound microorganism.

Item 22 is an article containing (a) a concentration agent comprising lanthanum and carbonate, wherein the concentration agent has a weight ratio of carbon to lanthanum that is at least 0.05; and (b) a microorganism bound to the concentration agent.

Item 23 is the article of item 22, wherein the microorganism is in a viable state.

Item 24 is the article of item 22 or 23, wherein the concentration agent comprises a plurality of particles.

Item 25 is the article of item 24, wherein the particles have an average diameter no greater than 100 micrometers.

Item 26 is the article of any one of items 22 to 25, wherein the concentration agent comprises lanthanum carbonate, lanthanum oxycarbonate, lanthanum hydroxycarbonate, or a mixture thereof.

Item 27 is the article of item 26, wherein the concentration agent comprises lanthanum carbonate that is anhydrous or hydrated.

Item 28 is the article of item 26, wherein the concentration agent comprises lanthanum oxycarbonate that is anhydrous or hydrated.

Item 29 is an article that includes a concentration agent and a porous matrix. The concentration agent contains both lanthanum and carbonate. The concentration agent has a weight ratio of carbon to lanthanum that is at least 0.05. The concentration agent is distributed on a surface of the porous matrix, throughout the porous matrix, or a combination thereof.

Item 30 is the article of item 29, wherein the concentration agent comprises a plurality of particles.

Item 31 is the article of item 30, wherein the particles are in the shape of platelets.

Item 32 is the article of any one of items 29 to 31, wherein the porous matrix comprises nonwoven fibers and an optional polymeric binder.

Item 33 is the article of item 32, wherein the nonwoven fibers comprise polymeric fibers, inorganic fibers, or a combination thereof.

Item 34 is the article of any one of items 29 to 31, wherein the porous matrix comprises a sintered polymeric material.

Item 35 is the article of item 34, wherein the sintered polymeric material comprises a sintered thermoplastic material.

Item 36 is the article of any one of items 29 to 35, wherein the porous matrix is in the form of a filter medium.

Item 37 is the article of any one of items 29 to 36, wherein the concentration agent comprises lanthanum carbonate, lanthanum oxycarbonate, lanthanum hydroxycarbonate, or a mixture thereof.

Item 38 is the article of item 37, wherein the concentration agent comprises lanthanum carbonate that is anhydrous or hydrated.

EXAMPLES

As used in the examples, all percentages are by weight unless otherwise specified. All of the examples were tested in duplicate unless indicated otherwise.

Materials

Unless otherwise specified, all reagents were purchased as standard products from either Sigma-Aldrich or VWR.

All bacterial and yeast cultures, which included *Escherichia coli* (ATCC 51813), *Staphylococcus aureus* (ATCC 6538), *Saccharomyces cerevisiae* (ATCC 201390), and *Listeria monocytogenes* (ATCC 51414), were purchased from American Type Culture Collection (Manassas Va.) unless otherwise stated. Unless otherwise specified, bacteria for testing were isolated from a streak culture prepared by streaking the culture on a Tryptic Soy Agar plate and incubating overnight at 37° C. according to standard microbiology practices. Yeast cultures for testing were isolated from streak culture prepared by streaking the culture on a Yeast Extract Peptone Dextrose Agar plate and incubating overnight at 30° C. according to standard microbiology practices.

As used herein, the term "Fiber 1" refers to fibrillated polyethylene fibers having a linear mass density of 1 denier that are commercially available under the trade designation FYBREL600 from Minifibers, Inc. (Johnson City, Tenn.).

As used herein, the term "Fiber 2" refers to chopped nylon fibers having a length of 2 inches and a linear mass density of 6 deniers that are commercially available from Minifibers, Inc. (Johnson City, Tenn.).

As used herein, the term "Fiber 3" refers to bi-component (ethylene vinyl acetate and polypropylene) fibers with 5 millimeter length having a linear mass density of 2 denier that are commercially available from Minifibers, Inc. (Johnson City, Tenn.).

As used herein, the term "Fiber 4" refers to glass fibers commercially available under the trade designation MICRO-STRAND 106-475 from Schuller Inc. (Denver, Colo.).

Lanthanum carbonate hydrate ($La_2(CO_3)_3 \cdot xH_2O$) was obtained from Alfa Aesar (Ward Hill, Mass.).

Lanthanum chloride ($LaCl_3$) was obtained from EM Science (Gibbstown, N.J.).

Lanthanum nitrate hexahydrate ($La(NO_3)_3 \cdot 6H_2O$) powder with a purity of 99.9% was obtained from Alfa Aesar (Ward Hill, Mass.).

Lanthanum oxide ($La_2O_3$) powder was obtained from Alfa Aesar (Ward Hill, Mass.).

Sodium bicarbonate ($NaHCO_3$) was purchased from EMD Chemicals, Inc. (Gibbstown, N.J.).

The term "latex binder" refers to a vinyl acetate emulsion with 50 weight percent solids that are commercially available under the trade designation AIRFLEX 600BP from Air Products Polymers (Allentown, Pa.).

The term "flocculant" refers to a polymeric material commercially available under then trade designation MP 9307 from Midsouth Chemical Co., Inc. (Ringgold La.).

"DI water" refers to deionized water with a resistivity of 18 megaohms that passed through a purification system commercially available under the trade designation MILLI-Q GRADIENT SYSTEM from Millipore (Waltham, Mass.).

The term "adsorption buffer" refers to a solution having a pH equal to 7.2. A 100× strength buffer contained 5 millimoles KCl, 1 millimole $CaCl_2$, 0.1 millimole $MgCl_2$, and 1 millimole $K_2HPO_4$ dissolved in DI water.

"BHI Broth" refers to a broth commercially available under the trade designation DIFCO BOVINE HEART INFUSION BROTH from Becton Dickinson (Sparks Md.) and prepared at 3.7 weight percent concentration according to the manufacturer's instructions.

"Butterfield's buffer" refers to a monobasic potassium phosphate buffer solution having a pH equal to 7.2±0.2. This buffer can be purchased from VWR (West Chester, Pa.).

"Tryptic Soy Agar plate" refers to a plate prepared according to manufacturer's instructions using 3 weight percent DIFCO Tryptic Soy Agar. The DIFCO Tryptic Soy Agar can be purchased from Benton Dickinson (Sparks, Md.).

"MOX plate" refers to a plate prepared using Oxford Medium modified for *Listeria* that is commercially available from Hardy Diagnostics (Santa Maria, Calif.).

"YPD agar plate" refers to an agar plate prepared according to manufacturer's instructions using 5 weight percent Yeast Extract Peptone Dextrose and 1.5% agar, which are both commercially available from Benton Dickinson (Sparks, Md.).

"*E. coli* plate" refers to a plate commercially available from 3M Company (Saint Paul, Minn.) under the trade designation 3M *E. COLI*/COLIFORM PETRIFILM PLATE.

"AC plate" refers to a plate commercially available from 3M Company (Saint Paul, Minn.) under the trade designation 3M AEROBIC COUNT PETRIFILM PLATE.

"YM plate" refers to a plate commercially available from 3M Company (Saint Paul, Minn.) under the trade designation 3M PETRIFILM YEAST AND MOLD PLATE.

The term "syringe" refers to one having a tip that is commercially available under the trade designation BD LUER-LOK". Such syringes can be purchased from VWR (West Chester, Pa.).

The term "filter holder" refers to a 13 millimeter filter holder that is commercially available under the trade designation SWINNEX from Millipore Corp. (Bedford, Mass.).

The terms "stomacher" refer respectively to a blender commercially available under the trade designation STOMACHER 400 Circulator Laboratory Blender that can be purchased from VWR (West Chester, Pa.). "Stomacher bag" refers to a polyethylene sample bags commercially available under the trade designation FILTRA-BAG that can be purchased from VWR.

The 0.5 McFarland Standard was prepared using a densitometer commerically available under the trade designation DENSICHEK from bioMerieux, Inc. (Durham, N.C.). A 0.5 McFarland number corresponds to bacterial concentration of approximately $1-1.5 \times 10^8$ CFUs/ml. The term CFU refers to colony forming units. McFarland standards are used as a reference to adjust the turbidity of bacterial suspensions so that the number of bacteria will be within a given range.

X-Ray Diffraction Analysis

Samples were examined directly on a zero background quartz insert. Reflection geometry data were collected in the form of a survey scan using a Philips vertical diffractometer, copper $K_\alpha$ radiation, and proportional detector registry of the scattered radiation. The diffractometer was fitted with variable incident beam slits, fixed diffracted beam slits, and a graphite diffracted beam monochromator. The survey scan was conducted from 5 to 80 degrees (2θ) using a 0.04 degree step size and 4 second dwell time. The X-ray generator was set at 45 kV and 35 mA. Powder diffraction files (PDF) were used for identification of phases present in the samples based on the reflections observed in the diffraction patterns.

Scanning Electron Microscopy (SEM) Imaging

Samples were mounted onto double-sided carbon tape adhered onto an aluminum stub. The mounted samples were coated with Au/Pd using a sputter coater (SEM Coating Unit PS3 from Ted Pella, Inc., (Irvine, Calif.)) to minimize charging effects during imaging. The coated samples were imaged in the secondary electron mode using a JEOL JSM-6400 Scanning Electron Microscope from JEOL USA, Inc. (Peabody, Mass.) with the following imaging conditions: 20 kV and 17 mm Working Distance (W.D.).

Lanthanum Analysis

The instrument used for elemental analysis was a Perkin Elmer Optima 8300 inductively-coupled plasma (ICP) optical emission spectrophotometer. The samples were analyzed against external calibration curves generated using acid-matched solution standards containing 0, 0.2, 0.5, and 1.0 parts per million (ppm) lanthanum. A 0.5 ppm quality-control standard was used to monitor the accuracy of the calibration curves during the analysis. A 0.5 ppm scandium solution was run in-line with the samples and standards to serve as an internal standard. In a typical analysis, 10 milligrams (mg) of sample was weighed to the nearest 0.01 mg into a polypropylene centrifuge tube and dissolved with 2 volume percent aqueous nitric acid. Once the solid had completely decomposed, the solutions were diluted to 50 mL with deionized water. Prior to analysis, the solutions were diluted an additional 100-fold by volume to bring the lanthanum concentrations within linear calibration range.

Carbon Analysis

Samples were analyzed for weight percent carbon by combustion using a LECO Model 932 CHNS elemental analyzer. The samples were run in at least triplicate and the results were reported as the averages of replicate determinations together with standard deviations. A calibration curve using a sulfamethazine standard was generated prior to analysis of samples. Unless otherwise noted, absolute standard deviation for carbon was less than +/−0.5 weight percent. The limit of detection for carbon was 0.50 weight percent.

Example 1

Concentration Agent 1

A lanthanum/carbonate-containing material (Concentration Agent 1) was prepared by adding equal volumes of an aqueous solution of 10 weight percent lanthanum nitrate ($La(NO_3)_3 \cdot 6H_2O$) drop-wise to an aqueous solution of 6 weight percent sodium bicarbonate ($NaHCO_3$) in a beaker while stirring constantly with a magnetic stir bar. Several minutes after the start of bicarbonate addition, bright white solids precipitated from solution. The solids were vacuum filtered and then washed with deionized water in a Buchner funnel fitted with a filter paper (WHATMAN filter paper #5). The solids were dried overnight in air at room temperature to give the lanthanum-containing Concentration Agent 1. X-ray diffraction analysis of this material (Concentration Agent 1) revealed the presence of a phase similar in structure to the mineral calkinsite (PDF: 6-0076). Based on scanning electron microscope (SEM) imaging of Concentration Agent 1, the particles had a plate-like morphology. The individual platelets were hundreds of nanometers in thickness and several microns in the planar dimension. These platelets tended to agglomerate into larger particulates up to tens of micrometers in size. The carbon content was 5.39 weight percent. The lanthanum content was 49.3 weight percent. The weight ratio of carbon to lanthanum was 0.109.

Example 2

Concentration Agent 2 (Concentration Agent 1 Heated at 300° C.)

Concentration Agent 1 as prepared in Example 1 was calcined within a quartz boat at 300° C. for one hour in air after a 30 minute ramp to 300° C. from room temperature in a box furnace (CARBOLITE RHF 1500 furnace from Carbolite LTD (Hope Valley, UK)). The resulting white powder (Concentration Agent 2) was analyzed by x-ray diffraction, indicating the presence of lanthanum carbonate (PDF: 6-0076 and/or 4-010-3609). The x-ray diffraction pattern showed strong orientation along the (200) and (400) planes as well as a broad set of reflections that may be assigned to disordered and/or small grained lanthanum oxycarbonate phases (PDF: 48-1113). Based on scanning electron microscope (SEM) imaging of the Concentration Agent 2, this material had a plate-like morphology similar to Concentration Agent 1 prepared in Example 1. The plate-like morphology is consistent with the strong orientation effects observed in the x-ray diffraction analysis. The carbon content was 6.73±0.16 weight percent. The lanthanum content was 57.9±0.8 weight percent. The weight ratio of carbon to lanthanum was 0.116±0.003.

Comparative Example 1

Concentration Agent 1 Heated at 550° C.

Concentration Agent 1 as prepared in Example 1 was calcined in a quartz boat at 550° C. for one hour in air after a 60 minute ramp to 550° C. from room temperature in a box furnace (CARBOLITE RHF 1500 furnace from Carbolite LTD (Hope Valley, UK)). The resulting white powder (Comparative Example 1) was found to contain lanthanum oxycarbonate (PDF:48-1113) as revealed by X-ray diffraction. SEM imaging of the material showed similar morphology and sizes as the material prepared in Example 2. The carbon content was 2.88±0.03 weight percent. The lanthanum content was 72.3 weight percent. The weight ratio of carbon to lanthanum was 0.040±0.0004.

Example 3

Concentration Agent 3

Concentration Agent 3 was commercially available lanthanum carbonate hydrate ($La_2(CO_3)_3 \cdot xH_2O$). Based on x-ray diffraction, this material contained lanthanite ($La_2(CO_3)_3 \cdot 8H_2O$) (PDF: 4-010-3609). Based on scanning electron microscope (SEM) imaging, Concentration Agent 4 had a plate-like morphology. The individual platelets were typically larger than one micrometer in thickness and tens of microns in the planar dimension. These platelets tended to agglomerate into larger particulates up to tens of micrometers in size. The carbon content was 5.31±0.12 weight percent. The lanthanum content was 44±1 weight percent. The weight ratio of carbon to lanthanum was 0.121±0.004.

Example 4

Concentration Agent 4 (Concentration Agent 3 Heated to 300° C.)

Concentration Agent 3 as described in Example 3 was calcined in a quartz boat at 300° C. for one hour in air after a 30 minute ramp to 300° C. from room temperature in a box furnace (CARBOLITE RHF 1500 furnace from Carbolite LTD (Hope Valley, UK)). The resulting white powder (Concentration Agent 4) had a similar X-ray diffraction pattern to the Concentration Agent 1. Based on scanning electron microscope (SEM) imaging, the morphology and microstructure was similar to that of Concentration Agent 3. The carbon content was 7.15±0.12 weight percent. The lanthanum content was 57.7±0.3 weight percent. The weight ratio of carbon to lanthanum was 0.124±0.002.

Comparative Example 2

Concentration Agent 3 Heated to 550° C.

Concentration Agent 3 as described in Example 3 was calcined in a quartz boat at 550° C. for one hour in air after a 60 minute ramp to 550° C. from room temperature in a box furnace (CARBOLITE RHF 1500 furnace from Carbolite LTD (Hope Valley, UK)). The resulting white powder (Comparative Example 2) contained lanthanum oxycarbonate (PDF:48-1113) based on x-ray diffraction. Scanning electron microscope (SEM) imaging of the material showed that it had a similar morphology and size to that of Concentration Agent 3. The carbon content was 2.86±0.04 weight percent. The lanthanum content was 72.3±0.8 weight percent. The weight ratio of carbon to lanthanum was 0.040±0.001.

Microorganism Suspension 1

Suspension of *E. Coli*

A streak culture of *Escherichia coli* (*E. coli*), a Gram negative bacterium, was used to prepare a 0.5 McFarland Standard in 3 mL of DI Water. The resulting bacterial stock, containing $10^8$ CFUs/ml, was serially diluted in an Adsorption buffer to obtain a bacterial suspension having $10^3$ microorganisms per milliliter of the suspension.

Example 5

Capture of *E. coli* on Example 2

Example 5 was prepared by adding a 1.0 mL volume of Microorganism Suspension 1 to a labeled, sterile 5 mL polypropylene tube that is commercially available under the trade designation BD FALCON from Becton Dickinson (Franklin Lakes, N.J.) containing 10 milligrams of Concentration Agent 2 prepared in Example 2. The capture efficiency is shown in Table 1.

Comparative Example 3

Capture of *E. coli* on Comparative Example 1

Comparative Example 3 was prepared in the same manner as Example 5 except that 10 milligrams of Comparative Example 1 were used instead of Concentration Agent 2. The capture efficiency is shown in Table 1.

Example 6

Capture of *E. coli* on Concentration Agent 3 from Example 3

Example 6 was prepared in the same manner as Example 5 except that 10 milligrams of Concentration Agent 3 described in Example 3 were used instead of Concentration Agent 2. The capture efficiency is shown in Table 1.

Example 7

Capture of *E. coli* on Concentration Agent 4

Example 7 was prepared in the same manner as Example 5 except that 10 milligrams of Concentration Agent 4 prepared in Example 4 were used instead of Concentration Agent 2. The capture efficiency is shown in Table 1.

Comparative Example 4

Capture of *E. coli* on Comparative Example 2

Comparative Example 4 was prepared in the same manner as Example 5 except that 10 milligrams of Comparative Example 2 were used instead of Concentration Agent 2. The capture efficiency is shown in Table 1.

Comparative Example C5

Capture of *E. coli* on $La_2O_3$

Comparative Example C5 was prepared in the same manner as Example 5 except 10 milligrams of lanthanum oxide ($La_2O_3$) was used instead of Concentration Agent 2. The capture efficiency is shown in Table 1.

Comparative Example C6

Capture of *E. coli* on $LaCl_3$

Comparative Example C6 was prepared in the same manner as Example 5 except 10 milligrams of lanthanum chloride ($LaCl_3$) was used instead of Concentration Agent 2. The capture efficiency is shown in Table 1.

Comparative Example C7

Capture of *E. coli* on $LaCl_3$

Comparative Example C7 was prepared by adding 10 mg of lanthanum chloride to 1 mL of filter sterilized DI water to prepare a 10 mg/mL (40 millimolar dispersion). Then, 5 microliters of this dispersion was added to 1 mL of Microorganism Suspension 1 in a sterile 5 mL tube. The lanthanum chloride concentration of Comparative Example C7 was 0.2 millimoles per mL of bacterial suspension. The capture efficiency is shown in Table 1.

Capture Efficiency for *E. coli*

Example 5-7 and Comparative Examples C3-C7

A Control Sample was prepared by adding 1.0 mL of Microorganism Suspension 1 to a labeled, sterile 5 mL polypropylene tube that is commercially available under the trade designation BD FALCON from Becton Dickinson (Franklin Lakes, N.J.). No concentration agent was added. One control sample contained 130 CFUs per mL *E. coli* and another contained 135 CFUs per mL *E. coli*.

The tubes containing Examples 5-7, Comparative Examples C3-C7, and the Control Samples were capped and mixed on a vortex mixer (THERMOLYNE MAXIMIX PLUS Vortex Mixer from Barnstead International (Dubuque Iowa)). The tubes were then agitated at room temperature (25° C.) for 10 minutes on a platform rocker (THERMO-LYNE VARI MIX Platform Rocker from Barnstead International) at 14 cycles per minute. The tube for Comparative Example C7 was agitated for an additional 20 minutes for a total of 30 minutes. After the agitation, each tube was allowed to settle for 10 minutes.

The settled materials were re-suspended in 1 mL sterile Butterfield's buffer, and plated on AC plates according to the manufacturer's instructions. The Control Samples were plated on AC plates in a similar manner. The plates were incubated at 37° C. for 18-20 hours and analyzed for colony counts using a 3M PETRIFILM Plate Reader (available from 3M Company (Saint Paul, Minn.)) according to the manufacturer's instructions. The Capture Efficiency (Efficiency) was equal to the number, in percent, of the microorganisms that were captured on the re-suspended material. The Capture Efficiency was determined from the number of colonies counted from the re-suspended material (Captured) and the number of colonies counted from the untreated Control Sample (Control) according to the following formula:

Capture Efficiency (%)=((Captured)/(Control))×100

The Capture Efficiency results for *E. coli* are shown in Table 1. Standard deviation in efficiency is less than 10% unless noted otherwise.

TABLE 1

Capture Efficiency for *E. coli*

| Example | Efficiency (%) |
|---|---|
| 5* | 93 |
| C3** | 74 |
| 6* | 54 |
| 7** | 89 |
| C4** | 51 (18% std. dev.) |
| C5* | 58 |
| C6* | 0 |
| C7* | 0 |

*Control sample for these examples contained 130 CFUs per mL *E. coli*
**Control sample for these examples contained 135 CFUs per mL *E. coli*

Microorganism Suspension 2

Suspension of *S. aureus*

A streak culture of *Staphylococcus aureus* (*S. aureus*), a Gram positive bacterium, was used to prepare a 0.5 McFarland Standard in 3 mL of DI Water. The resulting bacterial stock, containing $10^8$ CFUs/ml, was serially diluted in an Adsorption buffer to obtain a bacterial suspension having $10^3$ microorganisms per milliliter of the suspension.

Example 8

Capture of *S. aureus* on Concentration Agent 2

Example 8 was prepared by adding a 1.0 mL volume of Microorganism Suspension 2 to a labeled, sterile 5 mL polypropylene tube that is commercially available under the trade designation BD FALCON from Becton Dickinson (Franklin Lakes, N.J.) containing 10 milligrams of Concentration Agent 2 prepared in Example 2. The capture efficiency is shown in Table 2.

Comparative Example C8

Capture of *S. aureus* on Comparative Example 1

Comparative Example C8 was prepared in the same manner as Example 8 except that 10 milligrams of Comparative Example 1 were used instead of Concentration Agent 2. The capture efficiency is shown in Table 2.

Example 9

Capture of *S. aureus* on Concentration Agent 3

Example 9 was prepared in the same manner as Example 8 except that 10 milligrams of Concentration Agent 3 described in Example 3 were used instead of Concentration Agent 2. The capture efficiency is shown in Table 2.

Example 10

Capture of *S. aureus* on Concentration Agent 4

Example 10 was prepared in the same manner as Example 8 except that 10 milligrams of Concentration Agent 4 prepared in Example 4 were used instead of Concentration Agent 2. The capture efficiency is shown in Table 2.

Comparative Example C9

Capture of *S. aureus* on Comparative Example 2

Comparative Example C9 was prepared in the same manner as Example 8 except that 10 milligrams of Comparative Example 2 were used instead of Concentration Agent 2. The capture efficiency is shown in Table 2.

Comparative Example C10

Capture of *S. aureus* on $La_2O_3$

Comparative Example C10 was prepared in the same manner as Example 8 except 10 milligrams of lanthanum oxide ($La_2O_3$) was used instead of Concentration Agent 2. The capture efficiency is shown in Table 2.

Comparative Example C11

Capture of *S. aureus* on Concentration Agent $LaCl_3$

Comparative Example C11 was prepared in the same manner as Example 8 except 10 milligrams of lanthanum chloride ($LaCl_3$) was used instead of Concentration Agent 2. The capture efficiency is shown in Table 2.

Comparative Example C12

Capture of *S. aureus* on $LaCl_3$

Comparative Example C12 was prepared by adding 10 mg of lanthanum chloride to 1 mL of filter sterilized DI water to prepare a 10 mg/mL (40 millimolar dispersion).

Then, 5 microliters of this dispersion was added to 1 mL of Microorganism Suspension 2 in a sterile 5 mL tube. The lanthanum chloride concentration of Comparative Example C12 was 0.2 millimoles per mL of bacterial suspension. The capture efficiency is shown in Table 2.

Capture Efficiency for *S. aureus*

Example 8-10 and Comparative Examples C8-C12

A Control Sample was prepared by adding 1.0 mL of Microorganism Suspension 2 to a labeled, sterile 5 mL polypropylene tube that is commercially available under the trade designation BD FALCON from Becton Dickinson (Franklin Lakes, N.J.). No concentration agent was added. One control sample contained 140 CFUs per mL *S. aureus* and another contained 195 CFUs per mL *S. aureus*.

The tubes containing Examples 8-10, Comparative Examples C8-C12, and the Control Samples were capped and mixed on a vortex mixer (THERMOLYNE MAXIMIX PLUS Vortex Mixer from Barnstead International (Dubuque Iowa)). The tubes were then agitated at room temperature (25° C.) for 10 minutes on a platform rocker (THERMOLYNE VARI MIX Platform Rocker from Barnstead International) at 14 cycles per minute. The tube for Comparative Example C12 was agitated for an additional 20 minutes for a total of 30 minutes. After the agitation, each tube was allowed to settle for 10 minutes.

The settled materials were re-suspended in 1 mL sterile Butterfield's buffer, and plated on AC plates according to the manufacturer's instructions. The Control Samples were plated on AC plates in a similar manner. The plates were incubated at 37° C. for 18-20 hours and analyzed for colony counts using a 3M PETRIFILM Plate Reader (available from 3M Company (Saint Paul, Minn.)) according to the manufacturer's instructions. The Capture Efficiency was calculated as described above. The Capture Efficiency results for *S. aureus* are shown in Table 2. Standard deviation in efficiency is less than 10% unless noted otherwise.

TABLE 2

Capture Efficiency for *S. aureus*

| Example | Efficiency (%) |
|---|---|
| 8* | 100 |
| C8** | 60 (20% std. dev.) |
| 9* | 56 |
| 10** | 90 |
| C9** | 60 |
| C10* | 97 |
| C11* | 0 |
| C12* | 0 |

*Control sample for these examples contained 195 CFUs per mL *S. aureus*
**Control sample for these examples contained 140 CFUs per mL *S. aureus*

Example 11

Capture of Dilute *E. coli* on Concentration Agent 2

A streak culture of *E. coli* was used to make a 0.5 McFarland Standard in 3 mL of filtered sterilized water. The resulting bacterial stock, containing $1 \times 10^8$ CFU/mL, was serially diluted in water to obtain a bacterial suspension having approximately 100 CFU/mL. A diluted suspension was prepared by diluting the bacterial suspension 1:1000 with 100 mL of tap water to provide a dilute microorganism suspension having a concentration of approximately 10 CFUs total. A 1 mL volume of Adsorption buffer and 100 mL of the dilute microorganism suspension were added to a sterile 250 mL polypropylene conical bottom centrifuge tube obtained from VWR.

Concentration Agent 2 (100 mg) prepared in Example 2 was added to the dilute microorganism suspension. Duplicate samples were prepared. The tubes were capped and agitated at room temperature (25° C.) for 30 minutes on a platform rocker at 14 cycles/minute. After agitation, the content of the tubes were allowed to settle for about 30 minutes.

A volume of 99 mL was pipetted from each sample and discarded, leaving 1 mL of water containing the settled material. The settled material from each tube was removed with a pipette and inoculated onto separate *E. coli* plates. The plates were incubated at 37° C. for 18-20 hours and analyzed for colony counts using a 3M PETRIFILM Plate Reader (available from 3M Company (Saint Paul, Minn.)) according to the manufacturer's instructions. The Capture Efficiency was calculated to be 100 percent with a standard deviation less than 20 percent. The diluted microorganism suspension contained 3 CFUs per 100 mL. The average CFUs captured on Concentration Agent 2 was 3 CFUs.

Example 12

Porous Matrix Containing Concentration Agent 2 (5 Grams)

A fiber premix was prepared by mixing 30.0 grams of Fiber 1, 6.0 grams of Fiber 2, 4.5 grams of Fiber 3, and 3.0 grams of Fiber 4 with 4 liters of cold tap water in a 4 L blender (Waring Commercial Heavy Duty Blender, Model 37BL84 that is available from VWR Co. (Radnor, Pa.)) at medium speed for 90 seconds. The mixture was examined for uniform dispersion of the fibers without nits or clumps, and blended further as needed to break up any clumps. One liter of the fiber premix was then added to a 1 liter stainless steel beaker and mixed with an impeller mixer (Fisher Scientific STEDFAST Stirrer Model SL2400 available from ThermoFisher Scientific (Waltham, Mass.)) at a speed setting of 4 for five minutes. Then 1.0 g of latex binder was dispersed in about 25 mL of tap water in a 50 mL beaker and added to the mixture. The beaker was rinsed with about another 25 mL of tap water that was added to the mixture and mixed for about 2 minutes. In the same manner, 0.5 g of flocculant was dispersed in about 25 mL of tap water and added to the mixture while mixing, followed by the addition of about another 25 mL of rinse water from the beaker. The latex binder crashed out of solution onto the fibers and the liquid phase of the premix changed from cloudy to substantially clear. Then 5.0 grams of Concentration Agent 2 prepared in Example 2 was added and mixed on a vortex mixer for 1 minute.

A felt was prepared using a TAPPI pad maker apparatus obtained from Williams Apparatus (Watertown, N.Y.). This apparatus had a box measuring about 20 centimeters (8 inches) square and 20 centimeters (8 inches) high with a fine mesh screen at the bottom and a drain valve. The box was filled with tap water up to a height of about 1 centimeter above the screen. The particle-containing mixture was poured into the box and the valve was opened immediately which created a vacuum that pulled the water out of the box. The resulting wetlaid felt was approximately 3 millimeters thick.

The wetlaid felt was transferred from the apparatus onto a 20 centimeter square sheet of blotter paper (96-pound white paper from Anchor Paper (St. Paul, Minn.)). The felt was sandwiched between 2 to 4 layers of blotter paper, depending on the wetness of the sheet, and pressed between 2 reinforced screens in an air powered press set at 60 pounds per square inch (calculated to be about 12 pounds per square inch pressure exerted on the felt) for 1 to 2 minutes until no further water was observed being expelled. The pressed felt was then transferred onto a fresh sheet of blotter paper and placed in an oven (BLUE M STABIL-THERM oven, Model OV-560A2 from SPX Thermal Product Solutions (White Deer, Pa.)) set at 120° C. for about 40 minutes to remove residual water and cure the latex binder to form a porous matrix.

Example 13

Porous Matrix Containing Concentration Agent 2 (10 grams)

A porous matrix was prepared according to the procedure of Example 12 except that 10.0 grams of Concentration Agent 2 were added.

Microorganism Suspension 3

Suspension of L. monocytogenes

A streak culture of Listeria monocytogenes (L. monocytogenes) was used to prepare a 0.5 McFarland Standard in 3 mL of BHI Broth. The resulting bacterial stock, containing approximately $10^8$ CFUs per mL, was serially diluted in BHI broth to provide a bacterial suspension having approximately $10^3$ CFU per mL.

Example 14

Capture of L. monocytogenes on Porous Matrix/Concentration Agent of Example 12

A 14 millimeter diameter disc was die punched from the article of Example 12 and inserted into a filter holder (SWINNEX). A 3 mL syringe was used to deliver 1.5 mL of Microorganism Suspension 3 onto the disc sample in the filter holder. The filter holder was held over a container to collect the filtrate and filtration was completed in about 15 seconds. The capture efficiency is shown in Table 3.

Example 15

Capture of L. monocytogenes on Porous Matrix/Concentration Agent of Example 13

Example 15 was prepared and filtered according to the same procedure as described in Example 14 except the disc was die punched from the article of Example 13 instead of Example 12. The capture efficiency is shown in Table 3.

Capture Efficiency for L. monocytogenes on Examples 14-15

A 100 microliter volume from each filtrate obtained in Examples 14 and 15 was plated on MOX plates. A Control was prepared by plating 100 microliters of the unfiltered Microorganism Suspension 3 on a MOX plate. The disc articles from Examples 14 and 15 were removed from the filter holder after each filtration using surface sterilized forceps and placed on MOX plates with 100 microliters of Butterfield's buffer. All of the plates were incubated at 37° C. for 18-20 hours. Colonies were counted manually.

The Control sample had 3370 CFU/mL (5055 CFUs in 1.5 mL). All of the plated disc articles showed growth of L. monocytogenes indicating that the captured bacterial cells were viable.

Colony counts from the filtrates were used to calculate the Capture Efficiency for the disc articles as follows. Filtration Efficiency (Efficiency) was determined from the number of colonies counted from the filtrates (Filtrate Count) and the number of colonies counted from the unfiltered control sample (Control Count) according to the following formula:

Filtration Efficiency (%)=((Filtrate Count)/(Control Count))×100

Capture Efficiency (%)=100−Filtration Efficiency

Capture Efficiency Results are shown in Table 3.

TABLE 3

| Capture Efficiency of L. monocytogenes | |
|---|---|
| Example | Efficiency (%) |
| 14 | 63 |
| 15 | 83 |

Example 16

Removal of E. coli by Porous Matrix/Concentration Agent of Example 13

A streak culture of E. coli was used to prepare a 0.5 McFarland Standard in 3 mL of sterile DI water. The resulting bacterial stock containing $1\times10^8$ CFU/mL was serially diluted in DI water to obtain a bacterial suspension having approximately $10^5$ CFU/mL.

A 14 millimeter diameter disc was die-punched from the article of Example 13 and inserted into a filter holder (SWINNEX). A 3 mL syringe was used to deliver 1.0 mL of the bacterial suspension onto the disc in the filter. After filtering, the filtrate was collected, diluted 1:100 in DI water, and plated on E. coli plates. A Control sample was prepared by diluting the bacterial suspension having approximately $10^5$ CFU/mL by a factor of 1:100 in Butterfield's buffer and then plating 1 mL of the dilution. The plates were incubated at 37° C. for 18-20 hours. Colony counts were determined using a 3M PETRIFILM Plate Reader.

The Log Reduction Value (LRV) is an indication of bacterial removal capacity of a filtration matrix. The values were calculated based on the log value of the colony count (CFU/mL) in the control (Log Control Count) less the log value of colony count in the filtrate (Filtrate Count) according to the formula:

LRV=(Log$_{10}$(Control Count))−(Log$_{10}$(Filtrate Count))

The Control had an average colony count of 130,000 CFUs per mL (5.1 Log CFU per mL). No counts were observed in the filtrate resulting in a LRV of 5 for the disc article of Example 13.

Microorganism Suspension 4

Suspension of S. cerevisiae in Beer

A streak culture of Saccharomyces cerevisiae from a YPD agar plate was used to make a 0.5 McFarland Standard in 3 mL of beer (Michelob Golden Light Draft beer with 4.3% alcohol) purchased from a local retail store. The resulting yeast stock, containing approximately $10^6$ CFU/mL, was diluted serially in beer to obtain a yeast suspension containing $10^3$ CFU/mL. This sample is referred to as the Control yeast suspension. A spiked beer sample was prepared with a 1:100 dilution of the suspension inoculated into 100 mL of beer to provide 10 CFU/mL. This sample is referred to as the Spiked Beer Control or Microorganism Suspension 4.

Example 17

Concentration of *S. cerevisiae* on Porous Matrix/Concentration Agent of Example 12

A 14 mm disc was die-punched from Example 12 and inserted into a filter holder (SWINNEX). Microorganism Suspension 4 (100 mL) was delivered to the filter holder in five batches using a 20 mL syringe. After the entire sample passed through the porous matrix/concentration agent, the disc was transferred, using surface sterilized forceps, to an empty sterile 1.5 mL polypropylene micro-centrifuge tube (VWR, Catalog #89000-028). This is Example 17.

Then for determination of the capture efficiency of Example 17, 100 microliters of an enzyme solution and 50 microliters of an extractant solution from a sample preparation kit (3M CLEAN-TRACE SURFACE ATP SYSTEM from 3M Company (St. Paul, Minn.)) was added to the micro-centrifuge tube. The contents were mixed for 5 seconds at about 3200 revolutions per minute on a vortex mixer (VWR Fixed Speed vortex mixer from VWR (West Chester, Pa.)). The ATP signal of the sample was measured in relative light units (RLUs) for one minute at 10 sec intervals using a bench-top luminometer (20/20n Single Tube Luminometer from Turner Biosystems (Sunnyvale, Calif.)) equipped with 20/20n SIS software. Luminescence values were analyzed as described below. Direct detection of ATP was done without need for prior extraction/elution of the captured microorganism.

The background ATP level was determined by filtering 100 mL of unspiked beer (i.e., the beer without any *S. cerevisiae* added) through a disc die-cut from the porous matrix/concentration agent of Example 12. This Control Disc was processed according to the procedure described above for Example 17 and the ATP signal was measured.

The ATP signal for 100 microliters of only the beer (Unspiked Beer Background) was also measured. Unspiked Beer refers to the beer without any addition of *S. cerevisiae*. The background ATP signals were subtracted from the ATP signals of the beer containing test samples to calculate the Corrected ATP Signal values as shown in Table 4.

The ATP signals were also measured for the $10^3$ CFUs Control (100 microliters), and the unfiltered spiked beer sample (100 microliters). These samples were used as a $10^3$ CFUs Control and Spiked Beer Control samples, respectively.

The % ATP signal was calculated from the Corrected ATP Signal values for the controls according to the following equation:

% ATP Signal=(Corrected RLUs/RLUs from $10^3$ CFU Control)×100

Results are shown in Table 4.

TABLE 4

ATP signal measurements

| Sample | ATP Signal (RLUs) | Corrected ATP Signal (RLUs) | % ATP Signal of $10^3$ CFU control |
|---|---|---|---|
| Unspiked Beer Background | 747 | | |
| Control Disc | 826 | | |
| $10^3$ CFUs Control | 1420 | 673 | 100% |
| Spiked Beer Control | 980 | 233 | 34% |
| Example 17 | 1305 | 479 | 71% |

Yeast counts were determined by plating 1 mL of the 100 mL Spiked beer on Y/M plates according to the manufacturer's instructions and the sample had a total of 1350 CFUs of yeast cells.

Examples 18-19 and Comparative Example C13

Filtration of Beef Samples

A ground beef sample was prepared by adding 99 mL of Butterfield's buffer and 11 grams of ground beef (15% fat), purchased from a local grocery store, to a stomacher bag and processing on a stomacher according to the manufacturer's instructions at a speed of 230 rpm for 30 seconds.

Example 18 was prepared by delivering 10 mL of the ground beef sample with a 10 mL syringe to a 14 mm disc of Example 12 in a filter holder (SWINNEX). The syringe fit into the inlet port of filter holder and the plunger of the syringe was used to apply positive pressure to the sample until the entire sample passed through the matrix. The filtrate volume and filtration time are shown in Table 5.

Example 19 and Comparative Example C13 were prepared and tested in the same manner as described above for Example 18 except that Example 19 used a disc from Example 13 instead of Example 12, and Comparative Example C13 used a commercially available 0.22 micron polycarbonate (PC) WHATMAN filter (VWR) die punched to obtain a disc of 14 mm diameter.

TABLE 5

Filtration time for ground beef samples

| | Ground beef | |
|---|---|---|
| Example | Filtered Volume (mL) | Filtration Time (sec) |
| 18 | 10 | 14 |
| 19 | 10 | 13 |
| C13 | 0 | 30 |

The above data shows that the porous matrices/concentration agents of Examples 12 and 13 are somewhat less prone to clogging than a standard microbiology filter (polycarbonate filter) and also have greater filtration capacity when processing complex sample matrices.

Examples 20-21 and Comparative Example C14

Filtration of Soymilk Samples

Example 20 was prepared as follows. A soymilk sample was prepared by swirling 11 mL of soymilk (4.5 grams fat), purchased from a local grocery store, with 99 mL of Butterfield's buffer. A 10 mL sample was delivered with a 10 mL syringe to a 14 mm disc of Example 12 in a filter holder (SWINNEX). The syringe fit into the inlet port of filter holder and the plunger of the syringe was used to apply positive pressure to the sample until the entire sample passed through the matrix. The filtrate volume and filtration time are shown in Table 6.

Example 21 and Comparative Example C14 were prepared and tested in the same manner as described above for Example 20 except that Example 21 used a disc from Example 13 instead of Example 12, and Comparative Example C14 used a commercially available 0.22 micron polycarbonate (PC) WHATMAN filter (VWR) also 14 mm in diameter.

TABLE 6

Filtration time for soymilk samples

| | Soymilk | |
| --- | --- | --- |
| Example | Filtered Volume (mL) | Filtration Time (sec) |
| 20 | 10 | 45 |
| 21 | 9 | 55 |
| C14 | 0 | 30 |

The above data shows that the porous matrices/concentration agents of Examples 12 and 13 are somewhat less prone to clogging than a standard microbiology filter (polycarbonate filter) and also have greater filtration capacity when processing complex sample matrices.

What is claimed is:

1. A process for concentrating a microorganism, the process comprising:
    (a) providing a concentration agent comprising a plurality of particles of lanthanum/carbonate-containing materials, wherein the concentration agent has a weight ratio of carbon to lanthanum that is at least 0.05;
    (b) providing a fluid sample comprising the microorganism;
    (c) contacting the concentration agent with the fluid sample; and
    (d) binding the microorganism to the concentration agent to form a bound microorganism.

2. The process of claim 1, wherein the bound microorganism is in a viable state.

3. The process of claim 1, further comprising segregating the bound microorganism from the fluid sample.

4. The process claim 1, wherein the concentration agent further comprises a porous matrix, wherein the plurality of particles are distributed on a surface of the porous matrix, distributed throughout the porous matrix, or distributed both on the surface and throughout the porous matrix.

5. The process of claim 1, wherein the concentration agent comprises lanthanum carbonate, lanthanum oxycarbonate, lanthanum hydroxycarbonate, or a mixture thereof.

6. The process of claim 1, further comprising detecting the presence of the bound microorganism.

7. An article comprising:
    a concentration agent comprising a plurality of particles of lanthanum/carbonate-containing materials, wherein the concentration agent has a weight ratio of carbon to lanthanum that is at least 0.05; and
    a microorganism bound to the concentration agent.

8. The article of claim 7, wherein the microorganism is in a viable state.

9. The article of claim 7, wherein the concentration agent comprises lanthanum carbonate, lanthanum oxycarbonate, lanthanum hydroxycarbonate, or a mixture thereof.

10. An article comprising:
    a concentration agent comprising a plurality of particles of lanthanum/carbonate-containing materials, wherein the concentration agent has a weight ratio of carbon to lanthanum that is at least 0.05; and
    a porous matrix, wherein the concentration agent is distributed on a surface of the porous matrix, throughout the porous matrix, or a combination thereof.

11. The article of claim 10, wherein the porous matrix comprises nonwoven fibers and an optional polymeric binder.

12. The article of claim 10, wherein the porous matrix comprises a sintered polymeric material.

13. The article of claim 10, wherein the porous matrix is in the form of a filter medium.

* * * * *

UNITED STATES PATENT AND TRADEMARK OFFICE
CERTIFICATE OF CORRECTION

PATENT NO.       : 9,575,059 B2
APPLICATION NO.  : 14/400390
DATED            : February 21, 2017
INVENTOR(S)      : Manjiri Kshirsagar et al.

It is certified that error appears in the above-identified patent and that said Letters Patent is hereby corrected as shown below:

In the Specification

Column 17,
Line 24, delete "anthracia," and insert -- anthracis, --, therefor.

Column 18,
Line 12, delete "zymolose," and insert -- zymolyase, --, therefor.
Line 13, delete "enolysins." and insert -- endolysins. --, therefor.
Line 48, delete "adensosine" and insert -- adenosine --, therefor.

Column 27,
Line 8, delete "Iowa))." and insert -- IA)). --, therefor.

In the Claims

Column 35,
Line 34, in Claim 4, delete "process" and insert -- process of --, therefor.

Signed and Sealed this
Sixteenth Day of May, 2017

Michelle K. Lee
*Director of the United States Patent and Trademark Office*